(12) United States Patent
Pullen et al.

(10) Patent No.: US 7,312,916 B2
(45) Date of Patent: Dec. 25, 2007

(54) ELECTROPHORETIC MEDIA CONTAINING SPECULARLY REFLECTIVE PARTICLES

(75) Inventors: Anthony Edward Pullen, Belmont, MA (US); Gregg M. Duthaler, Needham, MA (US); Karl R. Amundson, Cambridge, MA (US); Benjamin Max Davis, San Francisco, CA (US)

(73) Assignee: E Ink Corporation, Cambridge, MA (US)

( * ) Notice: Subject to any disclaimer, the term of this patent is extended or adjusted under 35 U.S.C. 154(b) by 715 days.

(21) Appl. No.: 10/604,638

(22) Filed: Aug. 6, 2003

(65) Prior Publication Data

US 2004/0094422 A1 May 20, 2004

Related U.S. Application Data

(60) Provisional application No. 60/319,453, filed on Aug. 7, 2002.

(51) Int. Cl.
*G02B 26/00* (2006.01)
*G09G 3/34* (2006.01)
*G02F 11/00* (2006.01)

(52) U.S. Cl. .................. 359/296; 345/107; 204/600; 204/606; 204/616; 428/323; 428/379; 423/613; 356/28.5

(58) Field of Classification Search ............... 359/295, 359/296, 290, 223, 291; 345/107, 108, 86; 204/600, 606, 616; 428/323, 379; 423/613; 241/23, 39, 61; 356/28, 28.5, 436; 968/762
See application file for complete search history.

(56) References Cited

U.S. PATENT DOCUMENTS

| 2,766,478 A | 10/1956 | Raley, Jr. et al. |
| 2,800,457 A | 7/1957 | Green et al. |
| 3,036,388 A | 5/1962 | Tate |

(Continued)

FOREIGN PATENT DOCUMENTS

CH 563807 7/1975

(Continued)

OTHER PUBLICATIONS

Ackerman, "E Ink of Cambridge gets start-up funding", Boston Globe, Dec. 24, 1997, p. D4.

(Continued)

*Primary Examiner*—Loha Ben
(74) *Attorney, Agent, or Firm*—David J. Cole

(57) ABSTRACT

An electrophoretic medium (100) comprises at least one type of particle (108) suspended in a suspending fluid (106) and capable of moving therethrough on application of an electric field to the medium, the particles (108) including at least one electrophoretically mobile specularly reflective particle.

20 Claims, 7 Drawing Sheets

U.S. PATENT DOCUMENTS

| | | |
|---|---|---|
| 3,320,523 A * | 5/1967 | Trimble .................. 324/214 |
| 3,384,488 A | 5/1968 | Tulagin et al. |
| 3,389,194 A | 6/1968 | Somerville |
| 3,406,363 A | 10/1968 | Tate |
| 3,423,489 A | 1/1969 | Arens et al. |
| 3,460,248 A | 8/1969 | Tate |
| 3,512,876 A * | 5/1970 | Marks .................. 359/296 |
| 3,548,655 A * | 12/1970 | Rudd .................. 356/28.5 |
| 3,585,381 A | 6/1971 | Hodson et al. |
| 3,612,758 A | 10/1971 | Evans et al. |
| 3,639,133 A | 2/1972 | Linton |
| 3,668,106 A | 6/1972 | Ota |
| 3,670,323 A | 6/1972 | Sobel et al. |
| 3,680,961 A * | 8/1972 | Rudd .................. 356/335 |
| 3,756,693 A | 9/1973 | Ota |
| 3,767,392 A | 10/1973 | Ota |
| 3,772,013 A | 11/1973 | Wells |
| 3,792,308 A | 2/1974 | Ota |
| 3,806,893 A | 4/1974 | Ohnishi et al. |
| 3,841,732 A * | 10/1974 | Marks .................. 359/296 |
| 3,850,627 A | 11/1974 | Wells et al. |
| 3,870,517 A | 3/1975 | Ota et al. |
| 3,892,568 A | 7/1975 | Ota |
| 3,909,116 A | 9/1975 | Kohashi |
| 3,922,255 A | 11/1975 | Koestler et al. |
| 4,001,140 A | 1/1977 | Foris et al. |
| 4,041,481 A | 8/1977 | Sato |
| 4,045,327 A | 8/1977 | Noma et al. |
| 4,062,009 A | 12/1977 | Raverdy et al. |
| 4,068,927 A | 1/1978 | White |
| 4,071,430 A | 1/1978 | Liebert |
| 4,087,376 A | 5/1978 | Foris et al. |
| 4,088,395 A | 5/1978 | Giglia |
| 4,093,534 A | 6/1978 | Carter et al. |
| 4,104,520 A | 8/1978 | Lewis et al. |
| 4,123,206 A | 10/1978 | Dannelly |
| 4,123,346 A | 10/1978 | Ploix |
| 4,126,528 A | 11/1978 | Chiang |
| 4,126,854 A | 11/1978 | Sheridon |
| 4,143,103 A | 3/1979 | Sheridon |
| 4,143,472 A | 3/1979 | Murata et al. |
| 4,147,932 A | 4/1979 | Lewis |
| 4,149,149 A | 4/1979 | Miki et al. |
| 4,166,800 A | 9/1979 | Fong |
| 4,196,437 A | 4/1980 | Hertz |
| 4,201,691 A | 5/1980 | Asher et al. |
| 4,203,106 A | 5/1980 | Dalisa et al. |
| 4,211,668 A | 7/1980 | Tate |
| 4,218,302 A | 8/1980 | Dalisa et al. |
| 4,231,641 A | 11/1980 | Randin |
| 4,261,653 A | 4/1981 | Goodrich |
| 4,272,596 A | 6/1981 | Harbour et al. |
| 4,273,672 A | 6/1981 | Vassiliades |
| 4,279,632 A | 7/1981 | Frosch et al. |
| 4,285,801 A | 8/1981 | Chiang |
| 4,287,337 A | 9/1981 | Guglielmetti et al. |
| 4,298,448 A | 11/1981 | Muller et al. |
| 4,303,433 A | 12/1981 | Torobin |
| 4,305,807 A | 12/1981 | Somlyody |
| 4,311,361 A | 1/1982 | Somlyody |
| 4,314,013 A | 2/1982 | Chang |
| 4,324,456 A | 4/1982 | Dalisa |
| 4,368,952 A | 1/1983 | Murata et al. |
| 4,390,403 A | 6/1983 | Batchelder |
| 4,418,346 A | 11/1983 | Batchelder |
| 4,419,383 A | 12/1983 | Lee |
| 4,419,663 A | 12/1983 | Kohashi |
| 4,435,047 A | 3/1984 | Fergason |
| 4,438,160 A | 3/1984 | Ishikawa et al. |
| 4,439,507 A | 3/1984 | Pan et al. |
| 4,444,961 A | 4/1984 | Timm |
| 4,450,440 A | 5/1984 | White |
| 4,502,934 A | 3/1985 | Gazard et al. |
| 4,522,472 A | 6/1985 | Liebert et al. |
| 4,543,306 A | 9/1985 | Dubois et al. |
| 4,605,284 A | 8/1986 | Fergason |
| 4,620,916 A | 11/1986 | Zwemer et al. |
| 4,623,706 A | 11/1986 | Timm et al. |
| 4,643,528 A | 2/1987 | Bell, Jr. |
| 4,648,956 A | 3/1987 | Marshall et al. |
| 4,655,897 A | 4/1987 | DiSanto et al. |
| 4,666,673 A | 5/1987 | Timm |
| 4,707,080 A | 11/1987 | Fergason |
| 4,726,662 A | 2/1988 | Cromack |
| 4,732,830 A | 3/1988 | DiSanto et al. |
| 4,742,345 A | 5/1988 | DiSanto et al. |
| 4,746,917 A | 5/1988 | DiSanto et al. |
| 4,748,366 A | 5/1988 | Taylor |
| 4,772,102 A | 9/1988 | Fergason et al. |
| 4,776,675 A | 10/1988 | Takaochi et al. |
| 4,824,208 A | 4/1989 | Fergason et al. |
| 4,832,458 A | 5/1989 | Fergason et al. |
| 4,833,464 A | 5/1989 | DiSanto et al. |
| 4,850,919 A | 7/1989 | DiSanto et al. |
| 4,888,140 A | 12/1989 | Schlameus et al. |
| 4,889,603 A | 12/1989 | DiSanto et al. |
| 4,891,245 A | 1/1990 | Micale |
| 4,909,959 A | 3/1990 | Lemaire et al. |
| 4,919,521 A | 4/1990 | Tada et al. |
| 4,931,019 A | 6/1990 | Park |
| 4,947,219 A | 8/1990 | Boehm |
| 4,960,351 A | 10/1990 | Kendall, Jr. et al. |
| 5,009,490 A | 4/1991 | Kuono et al. |
| 5,017,225 A | 5/1991 | Nakanishi et al. |
| 5,040,960 A | 8/1991 | Shioya et al. |
| 5,041,824 A | 8/1991 | DiSanto et al. |
| 5,053,763 A | 10/1991 | DiSanto et al. |
| 5,057,363 A | 10/1991 | Nakanishi |
| 5,059,694 A | 10/1991 | Delabouglise et al. |
| 5,066,105 A | 11/1991 | Yoshimoto et al. |
| 5,066,559 A | 11/1991 | Elmasry et al. |
| 5,066,946 A | 11/1991 | DiSanto et al. |
| 5,070,326 A | 12/1991 | Yoshimoto et al. |
| 5,077,157 A | 12/1991 | DiSanto et al. |
| 5,082,351 A | 1/1992 | Fergason |
| 5,099,256 A | 3/1992 | Anderson |
| 5,105,185 A | 4/1992 | Nakanowatari et al. |
| 5,119,218 A | 6/1992 | Yoshimoto et al. |
| 5,128,226 A | 7/1992 | Hung |
| 5,128,785 A | 7/1992 | Yoshimoto et al. |
| 5,132,049 A | 7/1992 | Garreau et al. |
| 5,138,472 A | 8/1992 | Jones et al. |
| 5,149,826 A | 9/1992 | Delabouglise et al. |
| 5,151,032 A | 9/1992 | Igawa |
| 5,174,882 A | 12/1992 | DiSanto et al. |
| 5,177,476 A | 1/1993 | DiSanto et al. |
| 5,185,226 A | 2/1993 | Grosso et al. |
| 5,187,609 A | 2/1993 | DiSanto et al. |
| 5,204,424 A | 4/1993 | Roncali et al. |
| 5,213,983 A | 5/1993 | Gustafsson et al. |
| 5,216,416 A | 6/1993 | DiSanto et al. |
| 5,216,530 A | 6/1993 | Pearlman et al. |
| 5,223,115 A | 6/1993 | DiSanto et al. |
| 5,223,823 A | 6/1993 | DiSanto et al. |
| 5,247,290 A | 9/1993 | DiSanto et al. |
| 5,250,932 A | 10/1993 | Yoshimoto et al. |
| 5,250,938 A | 10/1993 | DiSanto et al. |
| 5,254,981 A | 10/1993 | DiSanto et al. |
| 5,260,002 A | 11/1993 | Wang |
| 5,266,098 A | 11/1993 | Chun et al. |
| 5,266,937 A | 11/1993 | DiSanto et al. |
| 5,268,448 A | 12/1993 | Buechner et al. |
| 5,270,843 A | 12/1993 | Wang |
| 5,272,238 A | 12/1993 | Garnier et al. |

| | | | | | |
|---|---|---|---|---|---|
| 5,276,113 A | 1/1994 | Hashiguchi et al. | 5,739,801 A | 4/1998 | Sheridon |
| 5,276,438 A | 1/1994 | DiSanto et al. | 5,744,283 A | 4/1998 | Spierings et al. |
| 5,279,511 A | 1/1994 | DiSanto et al. | 5,745,094 A | 4/1998 | Gordon, II et al. |
| 5,279,694 A | 1/1994 | DiSanto et al. | 5,751,268 A | 5/1998 | Sheridon |
| 5,293,528 A | 3/1994 | DiSanto et al. | 5,753,763 A | 5/1998 | Rao et al. |
| 5,296,974 A | 3/1994 | Tada et al. | 5,754,332 A | 5/1998 | Crowley |
| 5,298,833 A | 3/1994 | Hou | 5,759,671 A | 6/1998 | Tanaka et al. |
| 5,302,235 A | 4/1994 | DiSanto et al. | 5,760,761 A | 6/1998 | Sheridon |
| 5,303,073 A | 4/1994 | Shirota et al. | 5,767,826 A | 6/1998 | Sheridon et al. |
| 5,304,439 A | 4/1994 | DiSanto et al. | 5,777,782 A | 7/1998 | Sheridon |
| 5,315,312 A | 5/1994 | DiSanto et al. | 5,783,614 A | 7/1998 | Chen et al. |
| 5,326,484 A | 7/1994 | Nakashima et al. | 5,808,783 A | 9/1998 | Crowley |
| 5,344,594 A | 9/1994 | Sheridon | 5,825,529 A | 10/1998 | Crowley |
| 5,359,346 A | 10/1994 | DiSanto et al. | 5,828,432 A | 10/1998 | Shashidhar et al. |
| 5,360,689 A | 11/1994 | Hou et al. | 5,843,259 A | 12/1998 | Narang et al. |
| 5,380,362 A | 1/1995 | Schubert | 5,872,552 A | 2/1999 | Gordon, II et al. |
| 5,383,008 A | 1/1995 | Sheridon | 5,882,680 A | 3/1999 | Suzuki et al. |
| 5,389,945 A | 2/1995 | Sheridon | 5,894,367 A | 4/1999 | Sheridon |
| 5,402,145 A | 3/1995 | DiSanto et al. | 5,900,858 A | 5/1999 | Richley |
| 5,403,518 A | 4/1995 | Schubert | 5,914,806 A | 6/1999 | Gordon, II et al. |
| 5,411,398 A | 5/1995 | Nakanishi et al. | 5,930,026 A | 7/1999 | Jacobson et al. |
| 5,411,656 A | 5/1995 | Schubert | 5,961,804 A | 10/1999 | Jacobson et al. |
| 5,421,926 A | 6/1995 | Yukinobu et al. | 5,972,493 A | 10/1999 | Iwasaki et al. |
| 5,463,492 A | 10/1995 | Check, III | 6,005,791 A | 12/1999 | Gudesen et al. |
| 5,467,107 A | 11/1995 | DiSanto et al. | 6,005,817 A | 12/1999 | Gudesen et al. |
| 5,498,674 A | 3/1996 | Hou et al. | 6,014,247 A | 1/2000 | Winter et al. |
| 5,508,068 A | 4/1996 | Nakano | 6,017,584 A | 1/2000 | Albert et al. |
| 5,512,162 A | 4/1996 | Sachs et al. | 6,045,955 A | 4/2000 | Vincent |
| 5,528,399 A | 6/1996 | Izumi et al. | 6,054,071 A | 4/2000 | Mikkelsen, Jr. |
| 5,543,219 A | 8/1996 | Elwakil | 6,055,091 A | 4/2000 | Sheridon et al. |
| 5,552,679 A | 9/1996 | Murasko | 6,055,180 A | 4/2000 | Gudesen et al. |
| 5,556,583 A | 9/1996 | Tashiro et al. | 6,064,615 A | 5/2000 | Gudesen |
| 5,561,443 A | 10/1996 | DiSanto et al. | 6,064,784 A | 5/2000 | Whitehead et al. |
| 5,565,885 A | 10/1996 | Tamanoi | 6,067,185 A | 5/2000 | Albert et al. |
| 5,582,700 A | 12/1996 | Bryning et al. | 6,076,094 A | 6/2000 | Cohen et al. |
| 5,583,675 A | 12/1996 | Yamada et al. | 6,084,850 A | 7/2000 | Gudesen et al. |
| 5,597,889 A | 1/1997 | Takimoto et al. | 6,088,319 A | 7/2000 | Gudesen |
| 5,604,027 A | 2/1997 | Sheridon | 6,091,382 A | 7/2000 | Shioya et al. |
| 5,604,070 A | 2/1997 | Rao et al. | 6,097,531 A | 8/2000 | Sheridon |
| 5,610,455 A | 3/1997 | Allen et al. | 6,113,810 A | 9/2000 | Hou et al. |
| 5,614,340 A | 3/1997 | Bugner et al. | 6,117,294 A | 9/2000 | Rasmussen |
| 5,627,561 A | 5/1997 | Laspina et al. | 6,117,368 A | 9/2000 | Hou |
| 5,635,317 A | 6/1997 | Taniguchi et al. | 6,118,426 A | 9/2000 | Albert et al. |
| 5,638,103 A | 6/1997 | Obata et al. | 6,120,588 A | 9/2000 | Jacobson |
| 5,639,914 A | 6/1997 | Tomiyama et al. | 6,120,839 A | 9/2000 | Comiskey et al. |
| 5,643,506 A | 7/1997 | Rourke | 6,124,851 A | 9/2000 | Jacobson |
| 5,643,673 A | 7/1997 | Hou | 6,128,124 A | 10/2000 | Silverman |
| 5,650,199 A | 7/1997 | Chang et al. | 6,130,773 A | 10/2000 | Jacobson et al. |
| 5,650,247 A | 7/1997 | Taniguchi et al. | 6,130,774 A | 10/2000 | Albert et al. |
| 5,650,872 A | 7/1997 | Saxe et al. | 6,137,467 A | 10/2000 | Sheridon et al. |
| 5,654,367 A | 8/1997 | Takimoto et al. | 6,144,361 A | 11/2000 | Gordon, II et al. |
| 5,663,224 A | 9/1997 | Emmons et al. | 6,147,791 A | 11/2000 | Sheridon |
| 5,672,381 A | 9/1997 | Rajan | 6,171,464 B1 | 1/2001 | Chadha |
| 5,673,148 A | 9/1997 | Morris et al. | 6,172,798 B1 | 1/2001 | Albert et al. |
| 5,676,884 A | 10/1997 | Tiers et al. | 6,177,921 B1 | 1/2001 | Comiskey et al. |
| 5,688,584 A | 11/1997 | Casson et al. | 6,184,856 B1 | 2/2001 | Gordon, II et al. |
| 5,689,282 A | 11/1997 | Wolfs et al. | 6,225,971 B1 | 5/2001 | Gordon, II et al. |
| 5,691,098 A | 11/1997 | Busman et al. | 6,232,950 B1 | 5/2001 | Albert et al. |
| 5,693,442 A | 12/1997 | Weiss et al. | 6,239,896 B1 | 5/2001 | Ikeda |
| 5,694,224 A | 12/1997 | Tai | 6,241,921 B1 | 6/2001 | Jacobson et al. |
| 5,707,738 A | 1/1998 | Hou | 6,249,271 B1 | 6/2001 | Albert et al. |
| 5,707,747 A | 1/1998 | Tomiyama et al. | 6,252,564 B1 | 6/2001 | Albert et al. |
| 5,708,525 A | 1/1998 | Sheridon | 6,262,706 B1 | 7/2001 | Albert et al. |
| 5,709,976 A | 1/1998 | Malhotra | 6,262,833 B1 | 7/2001 | Loxley et al. |
| 5,714,270 A | 2/1998 | Malhotra et al. | 6,271,823 B1 | 8/2001 | Gordon, II et al. |
| 5,715,511 A | 2/1998 | Aslam et al. | 6,300,932 B1 | 10/2001 | Albert |
| 5,716,550 A | 2/1998 | Gardner et al. | 6,301,038 B1 | 10/2001 | Fitzmaurice et al. |
| 5,717,283 A | 2/1998 | Biegelsen et al. | 6,312,304 B1 | 11/2001 | Duthaler et al. |
| 5,717,514 A | 2/1998 | Sheridon | 6,312,971 B1 | 11/2001 | Amundson et al. |
| 5,717,515 A | 2/1998 | Sheridon | 6,323,989 B1 | 11/2001 | Jacobson et al. |
| 5,725,935 A | 3/1998 | Rajan | 6,327,072 B1 | 12/2001 | Comiskey et al. |
| 5,729,632 A | 3/1998 | Tai | 6,359,605 B1 | 3/2002 | Knapp et al. |
| 5,737,115 A | 4/1998 | Mackinlay et al. | 6,373,454 B1 | 4/2002 | Knapp et al. |

| | | |
|---|---|---|
| 6,373,461 B1 | 4/2002 | Hasegawa et al. |
| 6,376,828 B1 | 4/2002 | Comiskey |
| 6,377,387 B1 | 4/2002 | Duthaler et al. |
| 6,392,785 B1 | 5/2002 | Albert et al. |
| 6,392,786 B1 | 5/2002 | Albert |
| 6,413,790 B1 | 7/2002 | Duthaler et al. |
| 6,422,687 B1 | 7/2002 | Jacobson |
| 6,445,374 B2 | 9/2002 | Albert et al. |
| 6,445,489 B1 | 9/2002 | Jacobson et al. |
| 6,459,418 B1 | 10/2002 | Comiskey et al. |
| 6,473,072 B1 | 10/2002 | Comiskey et al. |
| 6,480,182 B2 | 11/2002 | Turner et al. |
| 6,498,114 B1 | 12/2002 | Amundson et al. |
| 6,504,524 B1 | 1/2003 | Gates et al. |
| 6,506,438 B2 | 1/2003 | Duthaler et al. |
| 6,512,354 B2 | 1/2003 | Jacobson et al. |
| 6,515,649 B1 | 2/2003 | Albert et al. |
| 6,518,949 B2 | 2/2003 | Drzaic |
| 6,521,489 B2 | 2/2003 | Duthaler et al. |
| 6,531,997 B1 | 3/2003 | Gates et al. |
| 6,535,197 B1 | 3/2003 | Comiskey et al. |
| 6,538,801 B2 | 3/2003 | Jacobson et al. |
| 6,545,291 B1 | 4/2003 | Amundson et al. |
| 6,580,545 B2 | 6/2003 | Morrison et al. |
| 6,639,578 B1 | 10/2003 | Comiskey et al. |
| 6,652,075 B2 | 11/2003 | Jacobson |
| 6,657,772 B2 | 12/2003 | Loxley |
| 6,664,944 B1 | 12/2003 | Albert et al. |
| D485,294 S | 1/2004 | Albert |
| 6,672,921 B1 | 1/2004 | Liang et al. |
| 6,680,725 B1 | 1/2004 | Jacobson |
| 6,683,333 B2 | 1/2004 | Kazlas et al. |
| 6,693,620 B1 | 2/2004 | Herb et al. |
| 6,704,133 B2 | 3/2004 | Gates et al. |
| 6,710,540 B1 | 3/2004 | Albert et al. |
| 6,721,083 B2 | 4/2004 | Jacobson et al. |
| 6,724,519 B1 | 4/2004 | Comiskey et al. |
| 6,727,881 B1 | 4/2004 | Albert et al. |
| 6,738,050 B2 | 5/2004 | Comiskey et al. |
| 6,750,473 B2 | 6/2004 | Amundson et al. |
| 6,753,999 B2 | 6/2004 | Zehner et al. |
| 6,788,449 B2 | 9/2004 | Liang et al. |
| 6,816,147 B2 | 11/2004 | Albert |
| 6,819,471 B2 | 11/2004 | Amundson et al. |
| 6,822,782 B2 | 11/2004 | Honeyman et al. |
| 6,825,068 B2 | 11/2004 | Denis et al. |
| 6,825,829 B1 | 11/2004 | Albert et al. |
| 6,825,970 B2 | 11/2004 | Goenaga et al. |
| 6,831,769 B2 | 12/2004 | Holman et al. |
| 6,839,158 B2 | 1/2005 | Albert et al. |
| 6,842,167 B2 | 1/2005 | Albert et al. |
| 6,842,279 B2 | 1/2005 | Amundson |
| 6,842,657 B1 | 1/2005 | Drzaic et al. |
| 6,864,875 B2 | 3/2005 | Drzaic et al. |
| 6,865,010 B2 | 3/2005 | Duthaler et al. |
| 6,866,760 B2 | 3/2005 | Paolini, Jr. et al. |
| 6,870,661 B2 | 3/2005 | Pullen et al. |
| 2002/0060321 A1 | 5/2002 | Kazlas et al. |
| 2002/0063661 A1 | 5/2002 | Comiskey et al. |
| 2002/0089735 A1* | 7/2002 | Albert et al. ............... 359/296 |
| 2002/0090980 A1 | 7/2002 | Wilcox et al. |
| 2002/0113770 A1* | 8/2002 | Jacobson et al. ........... 345/107 |
| 2002/0130832 A1 | 9/2002 | Baucom et al. |
| 2002/0180687 A1* | 12/2002 | Webber ...................... 345/107 |
| 2002/0180688 A1* | 12/2002 | Drzaic et al. .............. 345/107 |
| 2003/0011560 A1 | 1/2003 | Albert et al. |
| 2003/0020844 A1 | 1/2003 | Albert et al. |
| 2003/0102858 A1 | 6/2003 | Jacobson et al. |
| 2003/0132908 A1 | 7/2003 | Herb et al. |
| 2003/0151702 A1 | 8/2003 | Morrison et al. |
| 2003/0214695 A1 | 11/2003 | Abramson et al. |
| 2003/0222315 A1 | 12/2003 | Amundson et al. |
| 2004/0012839 A1 | 1/2004 | Cao et al. |
| 2004/0014265 A1 | 1/2004 | Kazlas et al. |
| 2004/0027327 A1 | 2/2004 | LeCain et al. |
| 2004/0075634 A1 | 4/2004 | Gates |
| 2004/0119681 A1 | 6/2004 | Albert et al. |
| 2005/0035941 A1 | 2/2005 | Albert et al. |

FOREIGN PATENT DOCUMENTS

| | | |
|---|---|---|
| DE | 195 00 694 | 8/1996 |
| EP | 0 281 204 A2 | 9/1988 |
| EP | 0 404 545 A2 | 12/1990 |
| EP | 0 443 571 A2 | 8/1991 |
| EP | 0 709 713 A2 | 5/1996 |
| EP | 1 145 072 B1 | 5/2003 |
| GB | 1 314 906 | 4/1973 |
| GB | 1465701 | 3/1977 |
| GB | 2 306 229 A | 4/1997 |
| JP | 53-073098 | 6/1978 |
| JP | 54-111368 A | 8/1979 |
| JP | 55-096922 A | 7/1980 |
| JP | 59-098227 A | 6/1984 |
| JP | 60-189731 A | 9/1985 |
| JP | 60-197565 A | 10/1985 |
| JP | 62-058222 A | 3/1987 |
| JP | 62-231930 A | 10/1987 |
| JP | 62-269124 A | 11/1987 |
| JP | 62-299824 A | 12/1987 |
| JP | 01-086117 A | 3/1989 |
| JP | 64-086116 | 3/1989 |
| JP | 64-086118 | 3/1989 |
| JP | 01-142537 A | 6/1989 |
| JP | 01-177517 A | 7/1989 |
| JP | 01-248182 A | 10/1989 |
| JP | 01-267525 A | 10/1989 |
| JP | 02-223934 A | 9/1990 |
| JP | 02-223935 A | 9/1990 |
| JP | 02-223936 A | 9/1990 |
| JP | 02-284124 A | 11/1990 |
| JP | 02-284125 A | 11/1990 |
| JP | 03-053224 A | 3/1991 |
| JP | 03-091722 A | 4/1991 |
| JP | 03-096925 A | 4/1991 |
| JP | 04-307512 A | 10/1992 |
| JP | 04-307523 A | 10/1992 |
| JP | 04-345133 A | 12/1992 |
| JP | 05-061421 A | 3/1993 |
| JP | 05-165064 A | 6/1993 |
| JP | 05-173194 A | 7/1993 |
| JP | 05-307197 A | 11/1993 |
| JP | 06-089081 A | 3/1994 |
| JP | 06-202168 A | 7/1994 |
| JP | 07-036020 A | 2/1995 |
| JP | 08-234176 A | 9/1996 |
| JP | 09-006277 A | 1/1997 |
| JP | 09-031453 A | 2/1997 |
| JP | 09-185087 A | 7/1997 |
| JP | 09-211499 A | 8/1997 |
| JP | 09-230391 A | 9/1997 |
| JP | 10-048673 A | 2/1998 |
| JP | 10-149118 A | 6/1998 |
| JP | 10-161161 A | 6/1998 |
| JP | 11-212499 A | 8/1999 |
| JP | 11-219135 A | 8/1999 |
| JP | 11-237851 A | 8/1999 |
| JP | 11-352526 A | 12/1999 |
| WO | WO 82/02961 | 9/1982 |
| WO | WO 95/33085 | 12/1995 |
| WO | WO 99/12170 | 3/1999 |
| WO | WO 99/26419 | 5/1999 |
| WO | WO 00/05704 | 2/2000 |
| WO | WO 00/36560 | 6/2000 |
| WO | WO 00/38000 | 6/2000 |
| WO | WO 00/67110 | 11/2000 |

| WO | WO 00/67327 | 11/2000 |
| WO | WO 01/07961 | 2/2001 |
| WO | WO 01/27690 | 4/2001 |

OTHER PUBLICATIONS

Amundson, K., et al., "Flexible, Active-Matrix Display Constructed Using a Microencapsulated Electrophoretic Material and an Organic-Semiconductor-Based Backplane", SID 01 Digest, 160 (Jun. 2001).
Antia, M., "Switchable Reflections Make Electronic Ink", Science, 285, 658 (1999).
Bach, U., et al., "Nanomaterials-Baed Electrochromics for Paper-Quality Displays", Adv. Mater, 14(11), 845 (2002).
Ballinger, D.O., "Magnetic recording paper is erasable", Electronics, Mar. 1, 1973, pp. 73-76.
Beilin, S., et al, "8.5: 2000-Character Electrophoretic Display", SID 86 Digest, 136 (1986).
Blazo, S.F., "High Resolution Electrophoretic Display with Photoconductor Addressing", SID Digest 1982, p. 152.
Bohnke et al., "Polymer-Based Solid Electrochromic Cell for Matrix-Addressable Display Devices." J. Electrochem. Soc., 138, 3612 (1991).
Boston Herald, "E Ink debuts in J.C. Penney Stores", May 3, 1999, p. 27.
Brenn, G., et al., "A new apparatus for the production of monodisperse sprays at high flow rates", Chem. Eng. Sci., 52, 237 (1997).
Brenn, G., et al., "Monodisperse Sprays for Various Purposes—Their Production and Characteristics", Part. Part. Syst. Charact., 13, 179 (1996).
Bryce, M.R., "Seeing through synthetic metals", Nature, 335. 12 (1988).
Chen, Y., et al., "A Comfortable Electronic Ink Display using a Foil-Based a-Si TFT Array", SID 01 Digest, 157 (Jun. 2001).
Chiang, A., "Conduction Mechanism of Charge Control Agents Used in Electrophoretic Display Devices", Proceeding of the S.I.D., 18, 275 (1977).
Chiang, A., et al., "A High Speed Electrophoretic Matrix Display", SID 80 Digest (1980), 114.
Chiang, A., et al., "A Stylus Writable Electrophoretic Display Device", SID 79 Digest (1979), 44.
Comiskey, B., et al., "An electrophoretic ink for all-printed reflective electronic displays", Nature, 394, 253 (1998).
Comiskey, B., et al., "Electrophoretic Ink: A Printable Display Material", SID 97 Digest (1997), p. 75.
Croucher, M.D., et al., "Electrophoretic Display: Materials as Related to Performance", Photog. Sci. Eng., 25, 80 (1981).
Dabbousi, B.O., et al., "Electroluminescence from CdSe quantum-dot/polymer composites", Appl. Phys. Lett., 66, 1316 (1995).
Dalisa, A.L., "Electrophoretic Display Technology", IEEE Trans. Electron Dev., ED-24, 827 (1977).
Danner, G.M. et al., "Reliability Performance for Microencapsulated Electrophoretic Displays with Simulated Active Matrix Drive", SID 03 Digest, 573 (2003).
Dobson, "Electronic Book is a Whole Library", Sunday Times (London), Feb. 25, 1996.
Drzaic, P., et al., "A Printed and Rollable Bistable Electronic Display", SID 98 Digest (1998) p. 1131.
Duthaler, G., et al., "Active-Matrix Color Displays Using Electrophoretic Ink and Color Filters", SID 02 Digest, 1374 (2002).
Egashira,. N., et al., "Solid electrochromic cell consisting of Lu-diphthalocyanine and lead fluoride", Proceedings of the SID, 28, 227 (1987).
Esen, C. et al., "Synthesis of Spherical Microcapsules by Photopolymerization in Aerosols", Colloid & Polymer Science, vol. 275, No. 2, 1997, pp. 131-137.
Fitzhenry, B., "Optical effects of adsorption of dyes on pigment used in electrophoretic image displays", Appl. Optics., 18, 3332 (1979).
Fitzhenry-Ritz, B., "Optical Properties of Electrophoretic Image Displays", Proceedings of the S.I.D., 22, 300 (1981).
Flaherty, "What Did Disappearing Ink Grow up to Be? Electronic Ink," The New York Times, May 6, 1999.

Franjinone et al., "The Art and Science of Microencapsulation", Technology Today, 1995, no page numbers.
Goodman, L.A., Passive Liquid Displays: Liquid Crystals, Electrophoretics and Electrochromics, Proceedings of S.I.D., 17, 30 (1976).
Guernsey, L., "Beyond Neon: Electronic Ink", New York Times, Jun. 3, 1999, p. G11.
Gutcho, M.H., Microcapsules and Microencapsulation Techniques, Noyes Data Corp., Park Ridge, NJ, (1976).
Hatano, T., et al., "18:3: Bistable Paper-White Display Device Using Cholesteric Liquid Crystals", SID 96 Digest, 269 (1996).
Heinzl, J., et al., "Ink-Jet Printing", Advances in Electronics and Electron Physics, 65, 91 (1985).
Henzen, A. et al., "Development of Active Matrix Electronic Ink Displays for Handheld Devices", SID 03 Digest, 176, (2003).
Huang, J., et al., "Photoluminescence and electroluminescence of ZnS:Cu nanocrystals in polymeric networks", Appl. Phys. Lett., 70, 2335 (1997).
Jacobson, J., et al., "The last book", IBM Systems J., 36, 457 (1997).
Ji, Y., et al., "P-50: Polymer Walls in Higher-Polymer-Content Bistable Reflective Cholesteric Displays", SID 96 Digest, 611 (1996).
Jin et al., "Optically Transparent, Electrically Conductive Composite Medium", Science, 255, 446 (1992).
Jo, G-R, et al., "Toner Display Based on Particle Movements", Chem. Mater, 14, 664 (2002).
Kazlas, P., et al., "12.1 SVGA Microencapsulated Electrophoretic Active Matrix Display for Information Applicances", SID 01 Digest, 152 (Jun. 2001).
Kitamura, T., et al., "Electrical toner movement for electronic paper-like display", Asia Display/IDW '01, p. 1517, Paper HCS1-1 (2001).
Lewis et al., "Gravitational, Inter-Particle and Particle-Electrode Forces in the Electrophoretic Display", Proceedings of the SID, 18, 235 (1977).
Luckham, P.F. et al., "The Controlled Flocculation of Particulate Dispersion Using Small Particles of Opposite Charge. III. Investigation of Floc Structure Using a Rheological Techniques", Colloids and Surfaces, 6 (1983), pp. 101-118.
Luckham, P.F. et al., "The Controlled Flocculation of Particulate Dispersions Using Small Particles of Opposite Charge. II. Investigation of Floc Structure Using a Freeze-Fracture Technique", Colloids and Surfaces, 6 (1983), pp. 83-95.
Matsumoto et al., "A Production Process for Uniform-Size Polymer Particles", Journal of Chemical Engineering of Japan, vol. 22, No. 6, 1989, pp. 691-694.
Matsumoto et al., "Production of Monodispersed Capsules", J. Microencapsulation, vol. 3, No. 1, 1986, pp. 25-31.
Matsumoto, S., et al., "Generation of Monodispersed Concentric Two Phase Droplets for Encapsulation," ICLASS-'82, Reports & Proc, 2nd Int. Conf. on Liquid Atomization & Spray Systems, pp. 63-67 (1982).
Murau, P., et al., "An Electrophoretic Radiographic Device", SID 79 Digest, (1979) pp. 46-47.
Murau, P., et al., "The understanding and elimination of some suspension instabilities in an electrophoretic display", J. Appl. Phys., 49, 4820 (1978).
Nakabu, S., et al., "The Development of Super-High Aperture Ratio with Low Electrically Resistive Material for High-Resolution TFT-LCDs", SID 99 Digest (1999), p. 732.
Nakamura, E., et al., "Development of Electrophoretic Display Using Microcapsulated Suspension," SID 98 Digest (1998), p. 1014.
Negroponte, N., et al., "Surfaces and Displays," Wired, Jan. 1997, p. 212.
O'Regan, B. et al., "A Low Cost, High-efficiency Solar Cell Based on Dye-sensitized colloidal TiO2 Films", Nature, vol. 353, Oct. 24, 1991, 773-740.
Ota, I., et al., "Developments in Electrophoretic Displays", Proceedings of the SID, 18, 243 (1977).
Ota, I., et al., "Electrophoretic display devices", Laser 75 Optoelectronics Conference Proceedings, 145 (1975).

Ota, I., et al., "Electrophoretic Image Display (EPID) Panel", Proceedings of the IEEE, 61, 832 (1973).

Pankove, "Color Reflection Type Display Panel", RCA Technical Notes, Mar. 1962, No. 535.

Pansu, B., et al., "Structures of Thin Layers of Hard Spheres: High Pressure Limit," J. Physique, 45, 331 (1984).

Pansu, B., et al., "Thin colloidal drystals: a series of structural transitions," J. Physique 44, 531 (1983).

Pearlstein, "Electroless Plating", in Lowenheim (ed.), Modern Electroplating, Wiley, New York (1976), pp. 710-747.

Peiranski, P., et al., "Thin Colloidal Crystals," Phys. Rev. Lett., 50, 900 (1983).

Peterson, I., "Rethinking Ink: Printing the Pages of an Electronic Book," Science News, 153, 396 (Jun. 20, 1998).

Pitt, M.G., et al., "Power Consumption of Microencapsulated Electrophoretic Displays for Smart Handheld Applications", SID 02 Digest, 1378 (2002).

Platt, C., "Digital Ink," Wired, May 1997, p. 162.

Ridley, B.A. et al., "All-Inorganic Field Effect Transistors by Printing," Science, 286, 746 (1999).

Saitoh, M., et al., "A newly developed electrical twisting ball display", Proceedings of the SID, 23, 249 (1982).

Sankus, "Electrophoretic Display Cell", Xerox Disclosure Journal, 6(3), 309 (1979).

Sheridon, N.K., et al., "The Gyricon—A Twisting Ball Display", Proceedings of the SID, 18, 289 (1977).

Shiffman, R.R., et al., "An Electrophoretic Image Display with Internal NMOS Address Logic and Display Drivers," Proceedings of the SID, 1984, vol. 25, 105 (1984).

Shimoda et al., "Multicolor Pixel Patterning of Light-Emitting Polymers by Ink-Jet Printing", SID 99 Digest, 376 (1999).

Shiwa, S., et al., "Electrophoretic Display Method Using Ionographic Technology," SID 88 Digest (1988), p. 61.

Singer, B., et al., "An X-Y Addressable Electrophoretic Display," Proceedings of the SID, 18, 255 (1977).

Van Winkle, D.H., et al., "Layering Transitions in Colloidal Crystals as Observed by Diffraction and Direct-Lattice Imaging", Phys. Rev. A, 34, 562 (1986).

Vance, D.W., "Optical Characteristics of Electrophoretic Displays", Proceedings of the SID, 18, 267 (1977).

Vandegaer, J.E. (ed.), "Microencapsulation Processes and Applications", pp. v-x, 1-180 (Plenum Press, New York 1974).

Vaz, N.A., et al., "Dual-frequency addressing of polymer-dispersed liquid-crystal films", J. Appl. Phys., 65, 5043 (1989).

Vincent, B. et al., "Adsorption of Small, Positive Particles onto Large, Negative Particles in the Presence of Polymer", J.C.S. Faraday 1, 1980, 76, pp. 665-682.

Webber, R., "Image Stability in Active-Matrix Microencapsulated Electrophoretic Displays", SID 02 Digest, 126 (2002).

White, R., "An Electrophoretic Bar Graph Display," Proceedings of the SID, 22, 173 (1981).

Wood, D., "An Electrochromic Renaissance?" Information Display, 18(3), 24 (Mar. 2002).

Yamaguchi, M., et al., "Equivalent Circuit of Ion Projection-Driven Electrophoretic Display," IEICE Transactions, 74, 4152 (1991).

Yamaguchi, Y., et al., "Toner display using insulative particles charged triboelectrically", Asia Display/IDW '01, p. 1729, Paper AMD4-4 (2001).

Yang, Y., et al., "A new architecture for polymer transistors", Nature, 372, 344 (1994).

Zehner, R. et al., "Drive Waveforms for Active Matrix Electrophoretic Displays", SID 03 Digest, 842 (2003).

Zollinger, "Structure of Simple Di- and Triarylmethine Dyes and their Aza Analogues," in Color Chemistry: Synthesis, Properties and Applications of Organic Dyes and Pigments, 2nd, Rev. Edition, VCH, Weinheim, 1991, p. 71-86.

Zurer, P., "Digital Ink Brings Electronic Books Closer," Chemical and Engineering News, Jul. 20, 1998, p. 12.

\* cited by examiner

ELECTROPHORETIC MEDIA CONTAINING SPECULARLY REFLECTIVE PARTICLES

CROSS REFERENCE TO RELATED APPLICATIONS

This application claims priority from Provisional Application Ser. No. 60/319,453, filed Aug. 7, 2002. The entire disclosure of this provisional application, and of all U.S. patent and applications mentioned below, is herein incorporated by reference.

BACKGROUND OF INVENTION

This invention relates to electrophoretic media containing pigments that are specularly reflective, and to electrophoretic displays containing such media for use in such displays.

Electrophoretic displays have been the subject of intense research and development for a number of years. Such displays can have attributes of good brightness and contrast, wide viewing angles, optical state bistability, and low power consumption when compared with liquid crystal displays. (The terms "bistable" and "bistability" are used herein in their conventional meaning in the art to refer to displays comprising display elements having first and second display states differing in at least one optical property, and such that after any given element has been driven, by means of an addressing pulse of finite duration, to assume either its first or second display state, after the addressing pulse has terminated, that state will persist for at least several times, for example at least four times, the minimum duration of the addressing pulse required to change the state of the display element.) Nevertheless, problems with the long-term image quality of these displays have prevented their widespread usage. For example, particles that make up electrophoretic displays tend to settle, resulting in inadequate service-life for these displays.

Numerous patents and applications assigned to or in the names of the Massachusetts Institute of Technology and E Ink Corporation have recently been published describing encapsulated electrophoretic media. Such encapsulated media comprise numerous small capsules, each of which itself comprises an internal phase containing electrophoretically-mobile particles suspended in a liquid suspension medium, and a capsule wall surrounding the internal phase. Typically, the capsules are themselves held within a polymeric binder to form a coherent layer positioned between two electrodes. Encapsulated media of this type are described, for example, in U.S. Pat. Nos. 5,930,026; 5,961,804; 6,017,584; 6,067,185; 6,118,426; 6,120,588; 6,120,839; 6,124,851; 6,130,773; 6,130,774; 6,172,798; 6,177,921; 6,232,950; 6,249,271; 6,252,564; 6,262,706; 6,262,833; 6,300,932; 6,312,304; 6,312,971; 6,323,989; 6,327,072; 6,376,828; 6,377,387; 6,392,785; 6,392,786; 6,413,790; 6,422,687; 6,445,374; 6,445,489; 6,459,418; 6,473,072; 6,480,182; 6,498,114; 6,504,524; 6,506,438; 6,512,354; 6,515,649; 6,518,949; 6,521,489; 6,531,997; 6,535,197; 6,538,801; 6,545,291; and 6,580,545; and U.S. Patent Applications Publication Nos. 2002/0019081; 2002/0021270; 2002/0053900; 2002/0060321; 2002/0063661; 2002/0063677; 2002/0090980; 2002/0106847; 2002/0113770; 2002/0130832; 2002/0131147; 2002/0145792; 2002/0171910; 2002/0180687; 2002/0180688; 2002/0185378; 2003/0011560; 2003/0011867; 2003/0011868; 2003/0020844; 2003/0025855; 2003/0034949; 2003/0038755; 2003/0053189; 2003/0076573; 2003/0096113 and 2003/0102858; and International Applications Publication Nos. WO 99/67678; WO 00/05704; WO 00/20922; WO 00/38000; WO 00/38001; WO 00/36560; WO 00/67110; WO 00/67327; WO 01/07961; and WO 01/08241.

Many of the aforementioned patents and applications recognize that the walls surrounding the discrete microcapsules in an encapsulated electrophoretic medium could be replaced by a continuous phase, thus producing a so-called polymer-dispersed electrophoretic display in which the electrophoretic medium comprises a plurality of discrete droplets of an electrophoretic fluid and a continuous phase of a polymeric material, and that the discrete droplets of electrophoretic fluid within such a polymer-dispersed electrophoretic display may be regarded as capsules or microcapsules even though no discrete capsule membrane is associated with each individual droplet; see for example, the aforementioned 2002/0185378. Accordingly, for purposes of the present application, such polymer-dispersed electrophoretic media are regarded as sub-species of encapsulated electrophoretic media.

A related type of electrophoretic display is a so-called "microcell electrophoretic display". In a microcell electrophoretic display, the charged particles and the suspending fluid are not encapsulated within microcapsules but instead are retained within a plurality of cavities formed within a carrier medium, typically a polymeric film. See, for example, International Applications Publication No. WO 02/01281, and published U.S. application Ser. No. 2002-0075556, both assigned to Sipix Imaging, Inc.

Known electrophoretic media, both encapsulated and unencapsulated, can be divided into two main types, referred to hereinafter for convenience as "single particle" and "dual particle" respectively. A single particle medium has only a single type of electrophoretic particle suspending in a colored suspending medium, at least one optical characteristic of which differs from that of the particles. (In referring to a single type of particle, we do not imply that all particles of the type are absolutely identical. For example, provided that all particles of the type possess substantially the same optical characteristic and a charge of the same polarity, considerable variation in parameters such as particle size and electrophoretic mobility can be tolerated without affecting the utility of the medium.) The optical property is typically color perceptible to the human eye, but may be another optical property, such as optical transmission, reflectance, luminescence or, in the case of displays intended for machine reading, pseudo-color in the sense of a change in reflectance of electromagnetic wavelengths outside the visible range. When such a medium is placed between a pair of electrodes, at least one of which is transparent, depending upon the relative potentials of the two electrodes, the medium can display the optical characteristic of the particles (when the particles are adjacent the electrode closer to the observer, hereinafter called the "front" electrode) or the optical characteristic of the suspending medium (when the particles are adjacent the electrode remote from the observer, hereinafter called the "rear" electrode, so that the particles are hidden by the colored suspending medium).

A dual particle medium has two different types of particles differing in at least one optical characteristic and a suspending fluid which may be uncolored or colored, but which is typically uncolored. The two types of particles differ in electrophoretic mobility; this difference in mobility may be in polarity (this type may hereinafter be referred to as an "opposite charge dual particle" medium) and/or magnitude. When such a dual particle medium is placed between the aforementioned pair of electrodes, depending upon the relative potentials of the two electrodes, the medium can display the optical characteristic of either set of particles, although the exact manner in which this is achieved differs depending upon whether the difference in mobility is in polarity or only in magnitude. For ease of illustration, consider an electrophoretic medium in which one type of particles are black and the other type white. If the two types of particles differ in polarity (if, for example, the black particles are positively charged and the white particles negatively charged), the particles will be attracted to the two different electrodes, so that if, for example, the front electrode is negative relative to the rear electrode, the black particles will be attracted to the front electrode and the white particles to the rear electrode, so that the medium will appear black to the observer. Conversely, if the front electrode is positive relative to the rear electrode, the white particles will be attracted to the front electrode and the black particles to the rear electrode, so that the medium will appear white to the observer.

If the two types of particles have charges of the same polarity, but differ in electrophoretic mobility (this type of medium may hereinafter to referred to as a "same polarity dual particle" medium), both types of particles will be attracted to the same electrode, but one type will reach the electrode before the other, so that the type facing the observer differs depending upon the electrode to which the particles are attracted. For example suppose the previous illustration is modified so that both the black and white particles are positively charged, but the black particles have the higher electrophoretic mobility. If now the front electrode is negative relative to the rear electrode, both the black and white particles will be attracted to the front electrode, but the black particles, because of their higher mobility, will reach it first, so that a layer of black particles will coat the front electrode and the medium will appear black to the observer. Conversely, if the front electrode is positive relative to the rear electrode, both the black and white particles will be attracted to the rear electrode, but the black particles, because of their higher mobility will reach it first, so that a layer of black particles will coat the rear electrode, leaving a layer of white particles remote from the rear electrode and facing the observer, so that the medium will appear white to the observer: note that this type of dual particle medium requires that the suspending fluid to sufficiently transparent to allow the layer of white particles remote from the rear electrode to be readily visible to the observer. Typically, the suspending fluid in such a display is not colored at all, but some color may be incorporated for the purpose of correcting any undesirable tint in the white particles seen therethrough.

As already mentioned, in typical single particle displays the medium comprises a plurality of white electrophoretically mobile particles of one polarity and optical characteristic suspended in a suspending fluid of a different optical characteristic which is darker and more light absorbing. In typical dual particle displays, the medium comprises a plurality of white electrophoretically mobile particles of one polarity and optical characteristic and a plurality of darker colored and more light absorbing particles such as carbon black which are electrophoretically mobile and have a second polarity and optical characteristic different from those the first white particles. In each case, the white particles are typically composed of surface modified titania. When the white titania particles are electrophoretically brought to the front electrode (switching to the white state), the particles pack in a manner which results in light being reflected in a Lambertian manner.

However, there are occasions when it may be desirable for an electrophoretic display to reflect light in other than a Lambertian manner. For example, if a display is to be mounted in a situation where it can only be observed from a limited range of angles, it may be desirable to use a display which concentrates reflected light into this limited range of angles. Similarly, although in many applications it is desirable that a display mimic the Lambertian reflectivity of paper, there may be some applications, for example in advertising, where it is desired to have a display capable of mimicking the reflectivity of a metal foil.

The following discussion of the present invention requires detailed consideration of scattering of light by the electrophoretic particles, and because of the way in which electrophoretic displays are normally viewed, conventional nomenclature regarding such scattering tends to be rather confusing. Most electrophoretic displays operate in a reflective mode in which light enters the display through a viewing surface, impinges upon the electrophoretic particles and is thence scattered back through the viewing surface; the light emerging from the viewing surface is seen by an observer and hence controls the appearance of the display. Since the viewing surface is normally regarded as the front (or visible) surface of the display, it is backscattered light which emerges from the front surface of the display. Furthermore, as discussed in more detail below, some of the light impinging upon the electrophoretic particles is forward scattered towards what is conventionally regarded as the rear surface of the display; this surface is typically occupied by the backplane of the display. For ease of comprehension, and to avoid incongruous references to backscattered light emerging from the front surface of the display and forward scattered light emerging from the rear surface, in the following discussion scattering towards the viewable surface of the display will be referred to as "viewable scattering", which scattering towards the rear or backplane surface of the display will be referred to as "backplane scattering". It should be noted that the aforementioned Provisional Application Ser. No. 60/319,453 uses the term "backscattering" loosely to refer to scattering to refer to scattering towards the rear or backplane surface, the type of scattering which is denoted "backplane scattering" herein.

The present inventors have realized that the reflectivity of the white states of paper-like electrophoretic displays can be enhanced by including specularly reflective particles in the electrophoretic medium. When light falls upon white (or other reflective) particles disposed adjacent the viewing surface of an electrophoretic display, some of the light is backplane scattered away from the viewing surface. This backplane scattered light may be absorbed by the colored suspending fluid in single particle displays or by the dark colored particles in dual particle displays. As a result, the backplane scattered light is lost and does not contribute to the brightness of the display.

It has now been realized that the aforementioned problems with electrophoretic displays can be reduced or eliminated by including in the display at least one type of particle which is specularly reflective (i.e. shows mirror-like reflectivity), and the present invention relates to electrophoretic media and displays comprising such specularly reflective particles.

SUMMARY OF INVENTION

Accordingly, this invention provides an electrophoretic medium comprising a plurality of at least one type of particle suspended in a suspending fluid and capable of moving therethrough on application of an electric field to the medium, the particles including at least one electrophoretically mobile specularly reflective particle.

The present medium may be of the single particle type and comprise a type of particle which is both specularly reflective and electrophoretically mobile in a colored suspending fluid. Alternatively, the present medium may be of the dual particle type and comprise a specularly reflective, electrophoretically mobile particle having a first optical characteristic, the medium further comprising a second type of particle which has a charge of opposite polarity to that of the first particle and is electrophoretically mobile, and has a second optical characteristic different from the first optical characteristic. In such a dual particle system, the suspending fluid may be colored or uncolored, but is typically substantially uncolored.

In a preferred embodiment of the present invention, specularly reflective particles are used to enhance the reflectivity of at least one of the two types of particles in a prior art dual particle electrophoretic medium by providing an "internal reflector" which reduces backplane scattering from one of the two types of particles. This preferred embodiment comprises at least three types of particles, the (first) specularly reflective type, a second type of particle which has a charge of the same polarity as that of the specularly reflective particle but typically has a higher electrophoretic mobility than the specularly reflective particle, and has a first optical characteristic, and a third type of particle which has a charge of the opposite polarity to that of the second type of particle, is electrophoretically mobile, and has a second optical characteristic different from the first optical characteristic. As described below with reference to FIGS. 3A and 3B, in this type of medium, when an electric field of appropriate polarity is applied to the medium, both the first and second types of particles move towards the viewing surface, but because of their higher electrophoretic mobility the second type of particles arrive first, leaving the first type of specularly reflective particles to form the internal reflector which reduces the effect of backplane scattering from the first type of particles.

This type of medium may further comprise a fourth type of particle which has a charge of the same polarity as that of the second type of particle, is electrophoretically mobile, and is specularly reflective.

The invention also provides a second type of dual particle system which comprises the specularly reflective particle and a second type of particle which has a charge of the same polarity as that of the specularly reflective particle but has a higher electrophoretic mobility than the specularly reflective particle.

This invention also extends to an electrophoretic display comprising an electrophoretic medium of the present invention and at least one electrode disposed adjacent to this medium.

BRIEF DESCRIPTION OF DRAWINGS

Preferred embodiments of the invention are shown in the accompanying drawings, in which.

DETAILED DESCRIPTION

The specularly reflective particles to be used in the present invention may be metal flakes or those of the "pearlescent" pigment family. The reflective particles may have a smooth surface and be highly specular, or may be brushed, ground, milled or processed to introduce Lambertian qualities to the reflection properties. When the specularly reflective particles are in the form of flakes, these flakes preferably have an aspect ratio (the ratio of average diameter to thickness) of at least about 3 and preferably in the range of about 5 to 25, and a major axis length of about 1 to about 15 μm.

In all the embodiments of the present invention, it is preferred that at least the non-reflective electrophoretically mobile particles bear a polymer coating, this polymer coating preferably being formed by one of the processes described in the aforementioned 2002/0185378.

Figure 1A:
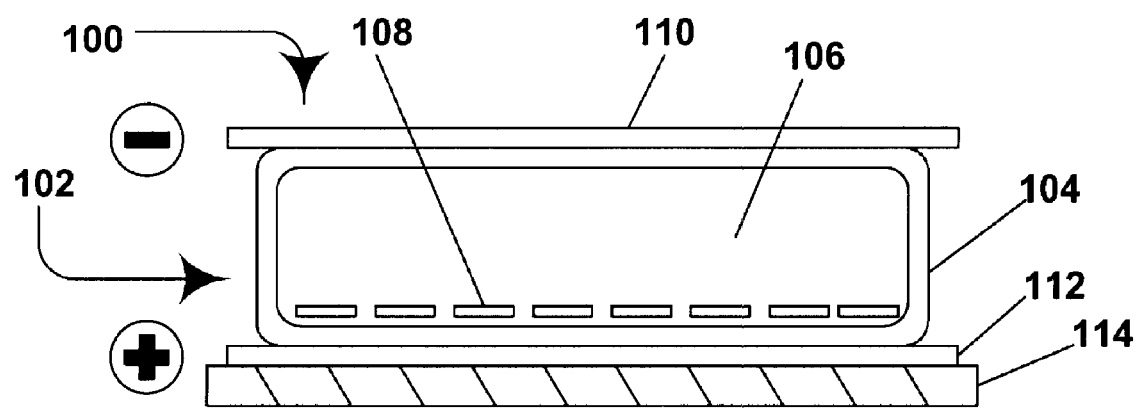
FIGS. 1A-1B are schematic side elevations showing two optical states of a first electrophoretic display of the present invention, in which the electrophoretic medium comprises a single type of particle, which is specularly reflective and electrophoretically mobile, in a colored suspending fluid.
Figure 1B:
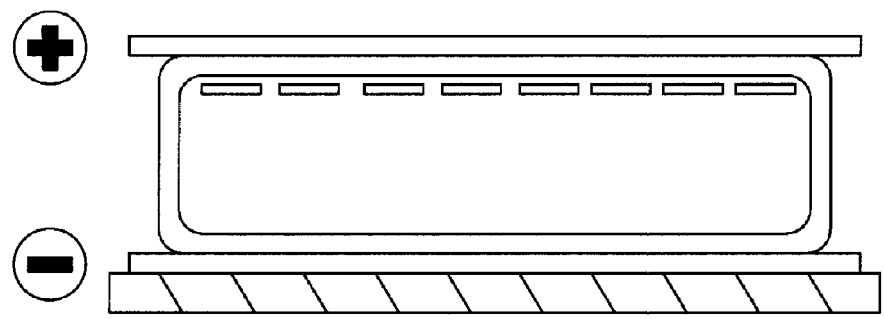

The first electrophoretic display (generally designated 100) of the invention shown in FIGS. 1A-1B comprises an encapsulated electrophoretic medium (generally designated 102) comprising a plurality of capsules 104 (only one of which is shown in FIGS. 1A-1B), each of which contains a suspending fluid 106 and dispersed therein a plurality of a single type of particle 108 which is specularly reflective and electrophoretically mobile. The elongated rectangular shape of the particles 108 illustrated in FIGS. 1A-1B is representative of the pigments chosen to introduce a specularly reflective property to the electrophoretic medium. Such pigments may be selected from, but are not limited to, metal-based pigments composed of aluminum, platinum, palladium, silver, gold, nickel, copper, chromium titanium, zinc, iron, stainless steel and tungsten with aspect ratios in the range of about 5 to about 25 with the major axis length of about 2 µm to about 10 µm. The particles 108 may also be selected from, but not limited to, molded or polished plastic chips, composite pigments such as those known to those skilled in the art as pearlescent-based pigments, composed of bismuth oxychloride (BiOCl), mica ($CaCO_3$) or titania ($TiO_2$) or ferric oxide ($Fe_2O_3$) particles adhered to the surface of mica or bismuth oxychloride with aspect ratios in the range of about 5 to about 25 with the major axis length of about 2 µm to about 10 µm. The particles 108 may have a polished surface in order to have a purely specular reflectivity or they may be brushed, ground, milled or otherwise processed to introduce surface roughness to add Lambertian reflectivity qualities. In the following description, it will be assumed that the particles 108 are negatively charged, although of course positively charged particles could also be used if desired.

The display 100 further comprises a common, transparent front electrode 110, which forms a viewing surface through which an observer views the display 100, and a plurality of discrete rear electrodes 112, each of which defines one pixel of the display 100 (only one rear electrode 112 is shown in FIGS. 1A-1B, although of course in practice a large number of electrodes 112 would be provided). For ease of illustration and comprehension, FIGS. 1A-1B show only a single microcapsule forming the pixel defined by rear electrode 112, although in practice a large number (20 or more) microcapsules are normally used for each pixel. The rear electrodes 112 are mounted upon a substrate 114, the electrodes 112 and the substrate 114 together forming the backplane of the display 100.

The suspending fluid 106 is colored such that the particles 108 lying in the positions shown in FIG. 1A adjacent the rear electrodes 112 are not visible to an observer viewing the display 100 via the front electrode 110. Since the colored suspending fluid 106 and the particles 108 render the electrophoretic medium 102 opaque, the rear electrodes 112 and the substrate 114 can be transparent or opaque since they are not visible through the opaque electrophoretic medium 102.

The capsules 104 and the particles 108 can be made in a wide range of sizes. However, in general it is preferred that the thickness of the capsules, measured perpendicular to the electrodes, be in the range of about 15 to 500 µm, while the particles 108 will typically have diameters in the range of about 0.25 to 2 µm.

FIG. 1A shows the display 100 with the front electrode 110 made negative relative to the rear electrode 112, as indicated by the negative sign adjacent the front electrode. Since the particles 108 are negatively charged, they will be attracted to the rear electrode 112, where they are hidden from an observer viewing the display 100 through the front electrode 110 by the colored suspending fluid 106. Accordingly, the pixel shown in FIG. 1A displays to the observer the color of the liquid 106, which for purposes of illustration will be assumed to be blue. (Although the display 100 is illustrated in FIGS. 1A-1B with the rear electrode at the bottom, in practice both the front and rear electrodes are typically disposed vertically for maximum visibility of the display 100. None of the displays described herein rely in any way upon gravity to control the movement of the particles; such movement under gravity is in practice far too slow to be useful for controlling particle movement.)

FIG. 1B shows the display 100 with the front electrode 110 made positive relative to the rear electrode 112, as indicated by the positive sign adjacent to the front electrode. Since the particles 108 are negatively charged, they will be attracted to the positively charged front electrode 110. Accordingly, the particles 108 move adjacent the front electrode 110, and the pixel displays the specularly reflective color of the particles 108. As already mentioned, the specular reflectivity provided by the particles 108 can cause the display to mimic the reflectivity of a metal or similar reflective ink and this type of reflectivity may be desirable in some instances, since it can be very effective in attracting the attention of observers, for example shoppers in a retail store. Such a display may also be useful as a micromirror in photonic devices.

In FIGS. 1A-1B, the capsules 104 are illustrated as being of substantially prismatic form, having a width (parallel to the planes of the electrodes) significantly greater than their height (perpendicular to these planes). This prismatic shape of the capsules 104 is deliberate. If the capsules 104 were essentially spherical, in the specularly reflective state shown in FIG. 1B, the particles 108 would tend to gather in the highest part of the capsule, in a limited area centered directly above the center of the capsule. The color seen by the observer would then be essentially the average of this central specularly reflective area and a blue annulus surrounding this central area, where the blue liquid 106 would be visible. Thus, even in this supposedly black state, the observer would see a light bluish color rather than a pure specularly reflective mirror-like image, and the contrast between the two extreme optical states of the pixel would be correspondingly limited. In contrast, with the prismatic form of microcapsule shown in FIG. 1B, the particles 108 cover essentially the entire cross-section of the capsule so that no, or at least very little blue liquid is visible, and the contrast between the extreme optical states of the capsule is enhanced. For further discussion on this point, and on the desirability of achieving close-packing of the capsules within the electrophoretic layer, the reader is referred to the aforementioned U.S. Pat. Nos. 6,067,185 and 6,392,785.

Figure 2A:
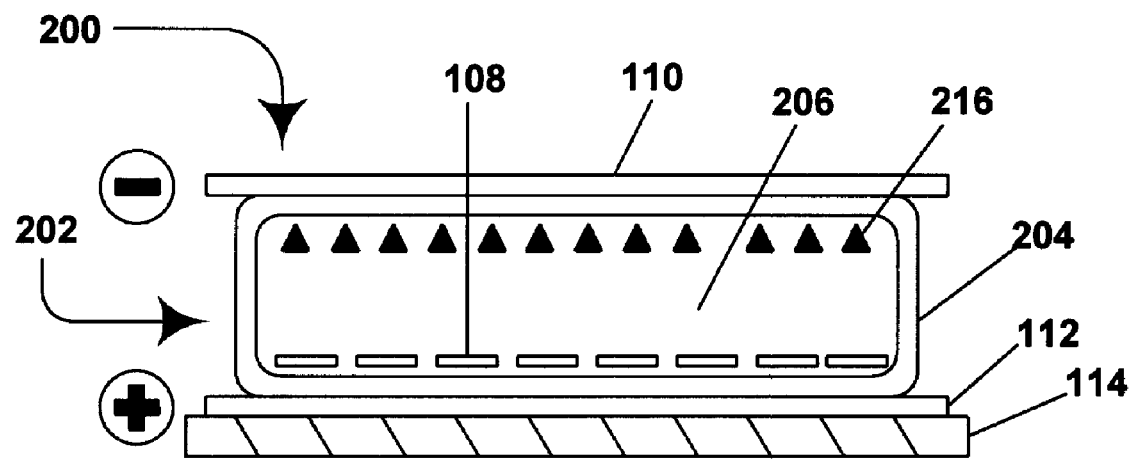
FIGS. 2A-2B are schematic side elevations showing two optical states of a second electrophoretic display of the present invention, in which the electrophoretic medium comprises one type of particle which is specularly reflective, electrophoretically mobile and bears a charge of one polarity, and a second type of particle which is at least, electrophoretically mobile and bears a charge of opposite polarity to that of the first type of particle, in an uncolored suspending medium.
Figure 2B:
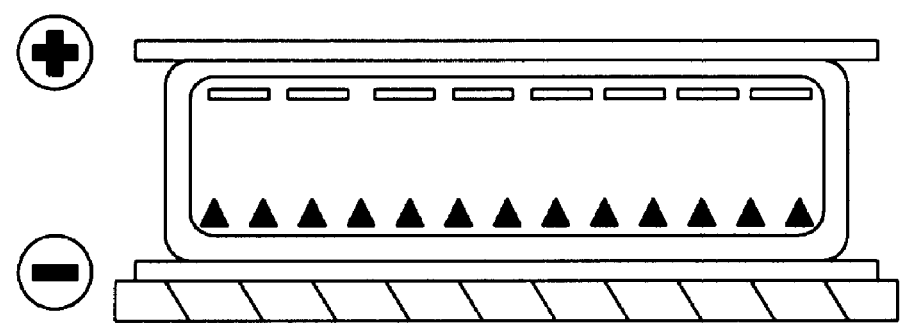

The second electrophoretic display (generally designated 200) of the invention shown in FIGS. 2A-2B comprises an encapsulated electrophoretic medium (generally designated 202) comprising a plurality of capsules 204, each of which contains a suspending liquid 206 and dispersed therein a plurality of specularly reflective, negatively charged particles 108 identical discussed to those in the first display 100 discussed above. The display 200 further comprises a front electrode 110, rear electrode 112, a substrate 114, all of which are identical to the corresponding integers in the first display 100. However, in addition to the specularly reflective particles 108, there are suspended in the uncolored suspending liquid 206 a plurality of positively charged, particles 216 that are at least electrophoretically mobile and have a charge polarity opposite to the first type of particle 108. For purposes of illustration only they will be assumed to be black. These particles could be either specularly reflective or non-specularly reflective (i.e. Lambertian). (The triangular shape of the particles 216, and the circular shapes of other particles discussed below, are used purely by way of illustration to enable the various types of particles to be distinguished easily in the accompanying drawings, and, except in the case of the flake-like particles 108 and the particles 418 mentioned below, in no way correspond to the physical forms of the actual particles, which are typically substantially spherical. However, we do not exclude the use of non-spherical particles in the present displays.)

FIG. 2A shows the display 200 with the front electrode 110 made negative relative to the rear electrode 112, as indicated by the negative sign adjacent to the front electrode 110. The positively charged black particles 216 are now attracted to the negatively charged front electrode 110, while the negatively charged, specularly reflective particles 108 are attracted to the positively charged rear electrode 112. Accordingly, the black particles 216 move adjacent the front electrode 110 and the specularly reflective particles 108 move adjacent the rear electrode 112, and the pixel displays the black color of particles 216.

FIG. 2B shows the display 200 with the front electrode 110 made positive relative to the rear electrode 112, as indicated by the positive sign adjacent to the front electrode 110. The negatively charged specularly reflective particles 108 are now attracted to the positively charged front electrode 110, while the positively charged black particles 216 are now attracted to the negatively charged rear electrode 112. Accordingly, the specularly reflective particles 108 move adjacent the front electrode 110, the black particles 216 move adjacent the rear electrode 112 and the pixel displays the specularly reflective color of the particles 108.

Figure 3A:
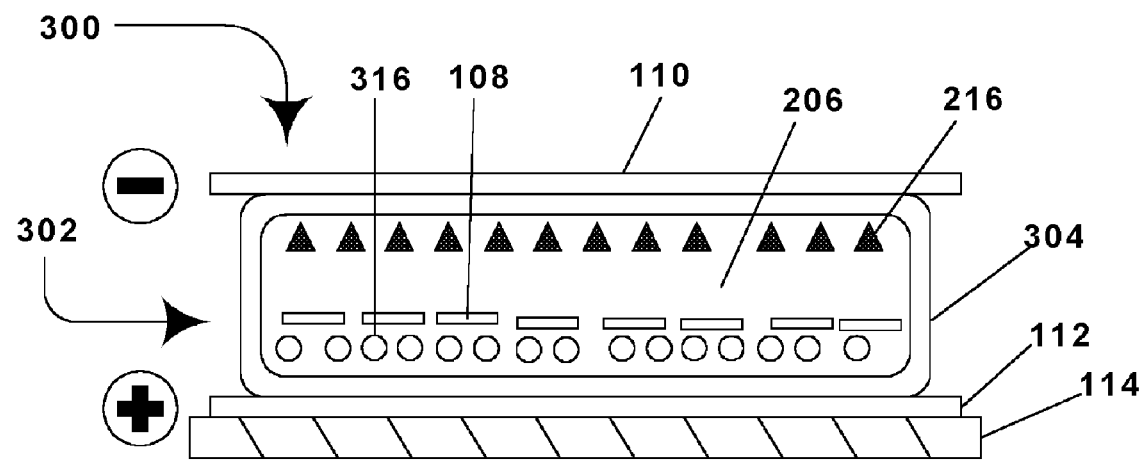
FIGS. 3A-3B are schematic side elevations showing two optical states of a third electrophoretic display of the present invention, in which the electrophoretic medium comprises one type of particle which is specularly reflective, electrophoretically mobile and bears a charge of one polarity, a second type of particle which is non-specularly reflective (hereinafter for convenience abbreviated "NSR"), electrophoretically mobile and bears a charge of the same polarity as that of the first type of particle, and a third type of particle which is at least electrophoretically mobile and bears a charge of opposite polarity to that of the first and second types of particles, in an uncolored suspending medium.
Figure 3B:
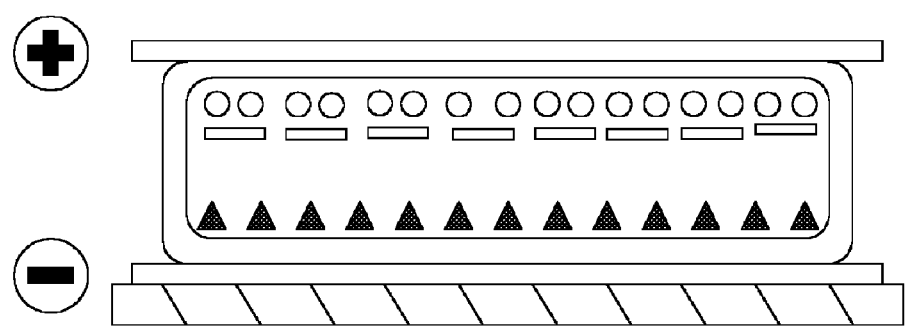

The third electrophoretic display (generally designated 300) of the invention shown in FIGS. 3A-3B comprises an encapsulated electrophoretic medium (generally designated 302) comprising a plurality of capsules 304, each of which contains a suspending liquid 206 and dispersed therein a plurality of specularly reflective, negatively charged particles 108 identical to those in the first display 100 discussed above, and a plurality of negatively charged, NSR particles 316, which for purposes of illustration will assumed to be white. The particles 316 have a higher electrophoretic mobility than the particles 108. The display 300 further comprises positively charged, black particles 216, a front electrode 110, rear electrode 112, a substrate 114, all of which are identical to the corresponding integers in the second display 200.

FIG. 3A shows the display 300 with the front electrode 110 made negative relative to the rear electrode 112, as indicated by the negative sign adjacent to the front electrode 110. The positively charged black particles 216 are now attracted to the negatively charged front electrode 110, while the negatively charged, specularly reflective particles 108 and negatively charged, NSR particles 326 are attracted to the positively charged rear electrode 112. Accordingly, the black particles 216 move adjacent the front electrode 110 and the specularly reflective particles 108 move adjacent the front electrode 110 and the pixel displays the black color of particles 216. (By virtue of their higher electrophoretic mobility, the particles 326 will normally lie adjacent the rear electrode 112, leaving a layer of the particles 108 facing the front electrode 110, as shown in FIG. 3A. However, the exact distribution of the particles 326 and 108 is irrelevant in FIG. 3A, since both set of particles are hidden by the black particles 216.)

FIG. 3B shows the display 300 with the front electrode 110 made positive relative to the rear electrode 112, as indicated by the positive sign adjacent to the front electrode 110. The specularly reflective particles 108 and the NSR white pigments 316 are now attracted to the positively charged front electrode 110, but, because of their greater electrophoretic mobility the particles 316 reach the front electrode first and form an essentially continuous layer of white particles immediately adjacent the front electrode 110, leaving the specularly reflective particles to form an "internal reflector" in the form of a specularly reflective layer immediately behind the layer of white particles 316. Such a specularly reflective layer is highly effective in reducing light losses due to backplane scattering from the white particles 316, and thus enhances the reflectivity of the white particles 316. The positively charged black particles 216 move adjacent the rear electrode 112. Thus, the pixel displays the white color of particles 316 with brightness enhancement by the presence of the reflective particles 108.

In the display 300, it is preferred that the specularly reflective particles 108 are of the same or similar polished color as that of the non-reflective particles 316, or they are polished white, silver or similarly colored solely to enhance the brightness of the particles 316 and to limit the amount of backplane scattered light that may be lost by absorption by the remaining components of the display 300, such as by the positively charged black particles 216.

Although in the display 300 the white particles 316 have been shown as having a higher electrophoretic mobility than the specularly reflective particles 108, this is not an essential feature of the present invention, and in the optical state shown in FIG. 3B, the particles 108 and 316 could be intermingled, as illustrated below in FIGS. 4A and 4B. Such intermingling of specularly reflective and NSR particles may be used to produce interesting optical effects.

The medium 300 shown in FIGS. 3A and 3B may be modified by omitting the particles 216 and providing a colored suspending fluid. The optical state of the display shown in FIG. 3B is essentially unaffected by this change, but in the state shown in FIG. 3A the color seen is that of the suspending fluid rather than that of the particles 216.

Figure 4A:
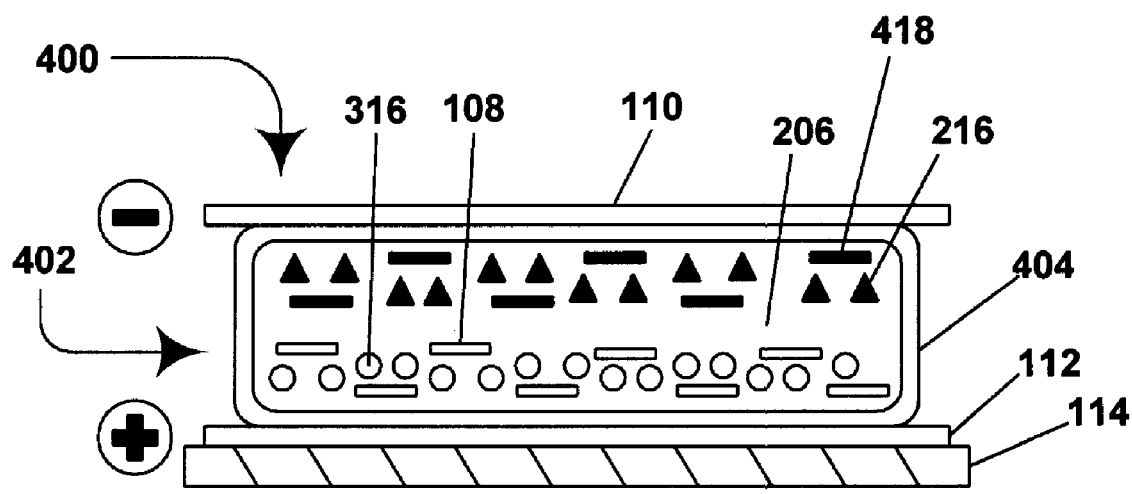
FIGS. 4A-4B are schematic side elevations showing two optical states of a fourth electrophoretic display of the present invention, in which the electrophoretic medium comprises one type of particle which is specularly reflective, electrophoretically mobile and bearing a charge of one polarity, a second type of NSR particle which is electrophoretically mobile and bears a charge of the same polarity as that of the first type of particle, a third type of particle which is specularly reflective, electrophoretically mobile and bears a charge of opposite polarity to that of the first and second types of particles, and a fourth type of NSR particle which is electrophoretically mobile and bears a charge of the same polarity as that of the third type of particle, in an uncolored suspending fluid.
Figure 4B:
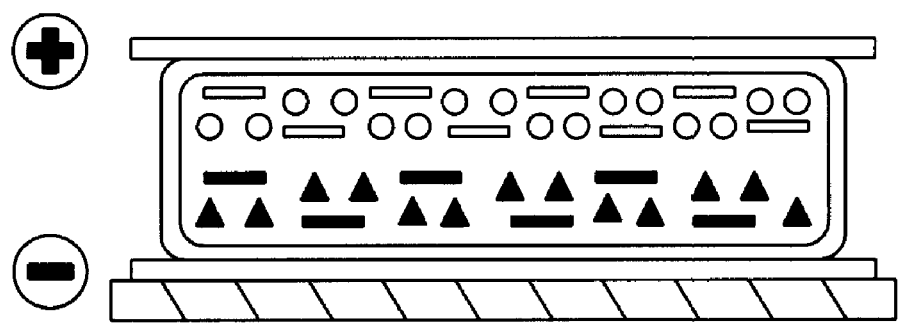

The fourth electrophoretic display (generally designated 400) of the invention shown in FIGS. 4A-4B comprises an encapsulated electrophoretic medium (generally designated 402) comprising a plurality of capsules 404, each of which contains a suspending liquid 206 and dispersed therein a plurality of specularly reflective, negatively charged particles 108 and white NSR particles 316 identical to those in the third display 100 discussed above, except that the particles 108 and 316 have substantially the same electrophoretic mobility. The display 400 further comprises a front electrode 110, rear electrode 112, a substrate 114, all of which are identical to the corresponding integers in the first display 100. As in the display 300, it is preferred that the specularly reflective particles 108 be of the same or similar polished color as that of the non-reflective particles 316, or be polished white, silver or similarly colored solely to enhance the brightness of the particles 316 and to limit the amount of backplane scattered light that may be lost by absorption by the remaining components of the display 300. However, in addition to the specularly reflective particles 108 and non-reflective particles 316, there are suspended in an uncolored suspending liquid 206, a plurality of positively charged, black particles 216, and a plurality of positively charged, specularly reflective particles 418, which for purposes of illustration will be assumed to be black. It is preferred that the specularly reflective black particles 418 are of the same or similar polished color as that of the non-reflective particles 216, or they are polished white, silver or similarly colored solely to enhance the brightness of the particles 216 and to limit the amount of backscattered light that may be lost by absorption by the remaining components of the display 400.

FIG. 4A shows the display 400 with the front electrode 110 made negative relative to the rear electrode 112, as indicated by the negative sign adjacent to the front electrode 110. The positively charged, non-reflective black particles 216 and the positively charged, specularly reflective particles 418, are now attracted to the negatively charged front electrode 110, while the negatively charged, specularly reflective particles 108 and negatively charge, non-reflective white particles 316 are attracted to the positively charged rear electrode 112. Accordingly, the black particles 216 and specularly reflective black particles 418 move adjacent the front electrode 110 and the specularly reflective particles 108 and non-reflective particles 316 move adjacent the rear electrode 112 and the pixel displays the black color of particles 216.

Finally, FIG. 4B shows the display 400 with the front electrode 110 made positive relative to the rear electrode 112, as indicated by the positive sign adjacent to the front electrode 110. The negatively charged specularly reflective particles 108 and the negatively charged, non-reflective white pigments 316, are now attracted to the positively charged front electrode 110, while the positively charged non-reflective black particles 216 and the positively charged specularly reflective particles 418 are attracted to the rear electrode 112. Accordingly, the specularly reflective particles 108 and white particles 316 move adjacent the front electrode 110 and the specularly reflective black particles 418 and black particles 216 move adjacent the rear electrode 112 and the pixel displays the white color of particles 316 with brightness enhancement by the presence of the reflective particles 108.

As already discussed, the use of a low concentration of reflective particles or flakes in an electrophoretic medium can help to eliminate problems due to backplane scattered light without adversely affecting other electro-optic properties of the medium. Furthermore, the use of such flakes enables a lower concentration of white particles to be used to achieve comparable bright states; this helps improve switching speed and reduce the cost of the display, as the white particles usually represents a significant expense in manufacturing such media. Alternatively, flakes can be used for high brightness applications, especially in color filter displays or ultra-bright monochrome displays.

Figure 5:
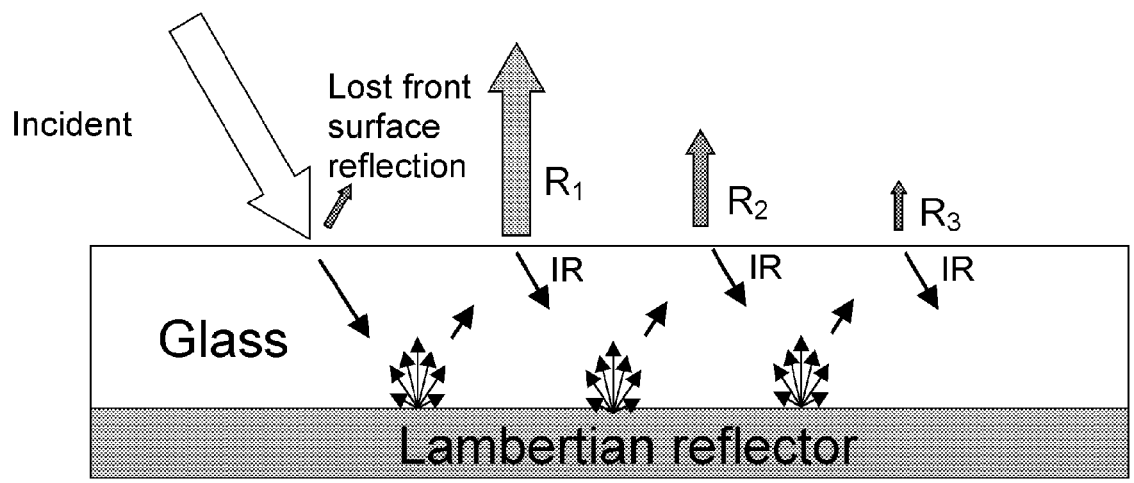
FIG. 5 illustrates schematically the reflections taking place within a typical electrophoretic display.
Figure 6:
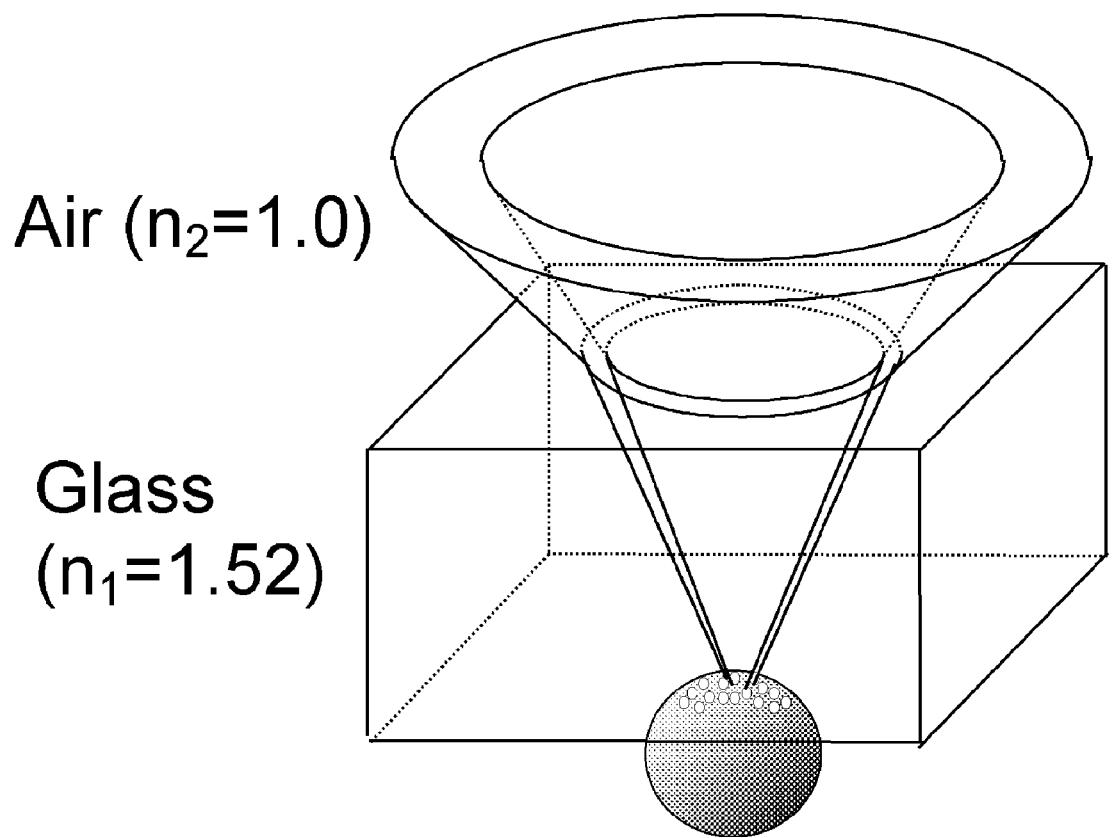
FIG. 6 illustrates schematically the manner in which viewably scattered light emerges from the viewing surface of a typical electrophoretic display.
Figure 7:
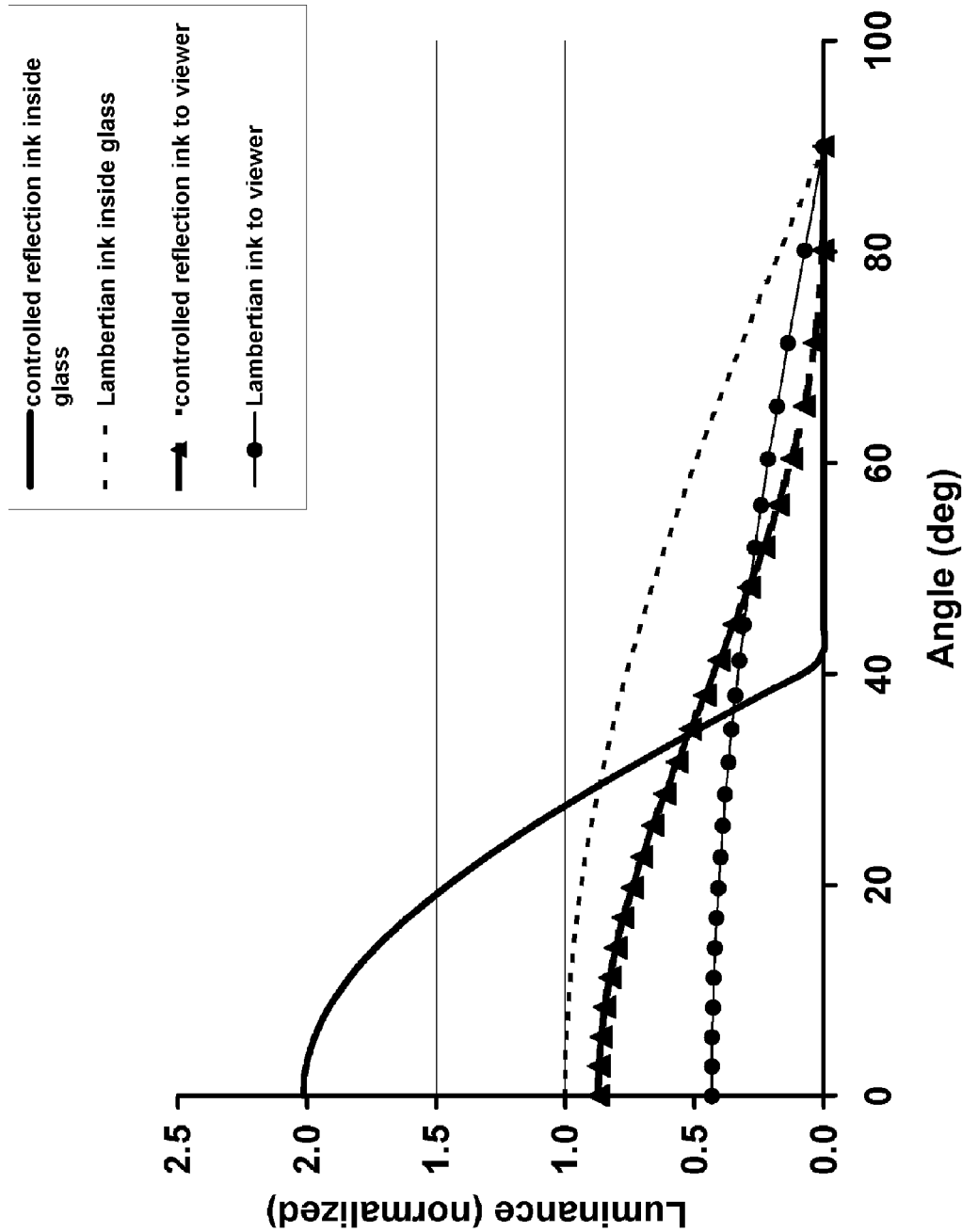
FIG. 7 shows the variation of luminance with viewing angle for electrophoretic displays using electrophoretic media having Lambertian and controlled reflection characteristics.

In preferred forms of the present invention, the particle compositions, loadings, switching waveforms, and particle packing of the display are adjusted to ensure that light reflects from the electrophoretic medium in a very controlled manner. Specifically, it is most desirable to reflect light from the medium such that all of the reflected light is able to pass out of the front (viewing) surface of the display without internal reflection and light recycling. As indicated in FIG. 5, some light that reflects from a Lambertian scattering medium disposed behind a window (either glass or plastic; such a window is normally present in an electrophoretic display to provide mechanical support and/or protection for the electrophoretic medium) undergoes internal reflection (indicated as "IR" in FIG. 5) at the air-window interface. The light that undergoes internal reflection is "recycled" and re-reflects off the scattering medium. By controlling the concentrations of particles and other switching parameters in accordance with the present invention, it is possible to direct most or all of the reflected light back into a cone whose half-angle roughly matches the critical angle of the air-window interface (see FIG. 6), thus ensuring that a very large fraction of the reflected light actually passes through the air-window interface without undergoing internal reflection (either partial or total). One can estimate the optical performance advantage of this controlled reflection profile, and the results appear in FIG. 7, from which it may be seen that a display in which the reflected light rays stay within the critical angle cone appears about twice as bright to an observer (looking perpendicular to the display, at 0° as plotted in FIG. 7), although the display still retains a substantially paper-like appearance.

Apart from the provision of the specularly reflective particles, the electrophoretic media and displays of the present invention may employ the same components and manufacturing techniques as in the aforementioned Massachusetts Institute of Technology and E Ink Corporation patents and applications. In view of the numerous different materials and manufacturing techniques which can be employed in such electrophoretic displays, the following Sections A-E are given by way of general guidance.

A. Electrophoretic Particles

There is much flexibility in the choice of particles for use in electrophoretic displays, as described above. For purposes of this invention, a particle is any component that is charged or capable of acquiring a charge (i.e., has or is capable of acquiring electrophoretic mobility), and, in some cases, this mobility may be zero or close to zero (i.e., the particles will not move). The particles may be neat pigments, dyed (laked) pigments or pigment/polymer composites, or any other component that is charged or capable of acquiring a charge. Typical considerations for the electrophoretic particle are its optical properties, electrical properties, and surface chemistry. The particles may be organic or inorganic compounds, and they may either absorb light or scatter light. The particles for use in the invention may further include scattering pigments, absorbing pigments and luminescent particles. The particles may be retroreflective, such as corner cubes, or they may be electroluminescent, such as zinc sulfide particles, which emit light when excited by an AC field, or they may be photoluminescent. Zinc sulfide electroluminescent particles may be encapsulated with an insulative coating to reduce electrical conduction. Finally, the particles may be surface treated so as to improve charging or interaction with a charging agent, or to improve dispersability.

One particle for use in electrophoretic displays of the invention is titania. The titania particles may be coated with a metal oxide, such as aluminum oxide or silicon oxide, for example. The titania particles may have one, two, or more layers of metal-oxide coating. For example, a titania particle for use in electrophoretic displays of the invention may have a coating of aluminum oxide and a coating of silicon oxide. The coatings may be added to the particle in any order.

The electrophoretic particle is usually a pigment, a polymer, a laked pigment, or some combination of the above. A neat pigment can be any pigment, and, usually for a light colored particle, pigments such as rutile (titania), anatase (titania), barium sulfate, kaolin, or zinc oxide are useful. Some typical particles have high refractive indices, high scattering coefficients, and low absorption coefficients. Other particles are absorptive, such as carbon black or colored pigments used in paints and inks. The pigment should also be insoluble in the suspending fluid. Yellow pigments such as diarylide yellow, Hansa yellow, and benzidin yellow have also found use in similar displays. Any other reflective material can be employed for a light colored particle, including non-pigment materials, such as metallic particles.

Useful neat pigments include, but are not limited to, PbCrO$_4$, Cyan blue GT 55-3295 (American Cyanamid Company, Wayne, N.J.), Cibacron Black BG (Ciba Company, Inc., Newport, Del.), Cibacron Turquoise Blue G (Ciba), Cibalon Black BGL (Ciba), Orasol Black BRG (Ciba), Orasol Black RBL (Ciba), Acetamine Black, CBS (E. I. du Pont de Nemours and Company, Inc., Wilmington, Del., hereinafter abbreviated "du Pont"), Crocein Scarlet N Ex (du Pont) (27290), Fiber Black VF (du Pont) (30235), Luxol Fast Black L (du Pont) (Solv. Black 17), Nirosine Base No. 424 (du Pont) (50415 B), Oil Black BG (du Pont) (Solv. Black 16), Rotalin Black RM (du Pont), Sevron Brilliant Red 3 B (du Pont); Basic Black DSC (Dye Specialties, Inc.), Hectolene Black (Dye Specialties, Inc.), Azosol Brilliant Blue B (GAF, Dyestuff and Chemical Division, Wayne, N.J.) (Solv. Blue 9), Azosol Brilliant Green BA (GAF) (Solv. Green 2), Azosol Fast Brilliant Red B (GAF), Azosol Fast Orange RA Conc. (GAF) (Solv. Orange 20), Azosol Fast Yellow GRA Conc. (GAF) (13900 A), Basic Black KMPA (GAF), Benzofix Black CW-CF (GAF) (35435), Cellitazol BNFV Ex Soluble CF (GAF) (Disp. Black 9), Celliton Fast Blue AF Ex Conc (GAF) (Disp. Blue 9), Cyper Black IA (GAF) (Basic Black 3), Diamine Black CAP Ex Conc (GAF) (30235), Diamond Black EAN Hi Con. CF (GAF) (15710), Diamond Black PBBA Ex (GAF) (16505); Direct Deep Black EA Ex CF (GAF) (30235), Hansa Yellow G (GAF) (11680); Indanthrene Black BBK Powd. (GAF) (59850), Indocarbon CLGS Conc. CF (GAF) (53295), Katigen Deep Black NND Hi Conc. CF (GAF) (15711), Rapidogen Black 3 G (GAF) (Azoic Black 4); Sulphone Cyanine Black BA-CF (GAF) (26370), Zambezi Black VD Ex Conc. (GAF) (30015); Rubanox Red CP-1495 (The Sherwin-Williams Company, Cleveland, Ohio) (15630); Raven 11 (Columbian Carbon Company, Atlanta, Ga.), (carbon black aggregates with a particle size of about 25 µm), Statex B-12 (Columbian Carbon Co.) (a furnace black of 33 µm average particle size), Greens 223 and 425 (The Shepherd Color Company, Cincinnati, Ohio 45246); Blacks 1, 1G and 430 (Shepherd); Yellow 14 (Shepherd); Krolor Yellow KO-788-D (Dominion Colour Corporation, North York, Ontario; "KROLOR" is a Registered Trade Mark); Red Synthetic 930 and 944 (Alabama Pigments Co., Green Pond, Ala. 35074), Krolor Oranges KO-786-D and KO-906-D (Dominion Colour Corporation); Green GX (Bayer); Green 56 (Bayer); Light Blue ZR (Bayer); Fast Black 100 (Bayer); Black 444 (Shepherd); Light Blue 100 (Bayer); Light Blue 46 (Bayer); Yellow 6000 (First Color Co., Ltd., 1236-1, Jwungwang-dong, Shihung, Kyounggi-do, Korea), Blues 214 and 385 (Shepherd); Violet 92 (Shepherd); and chrome green.

Particles may also include laked, or dyed, pigments. Laked pigments are particles that have a dye precipitated on them or which are stained. Lakes are metal salts of readily soluble anionic dyes. These are dyes of azo, triphenylmethane or anthraquinone structure containing one or more sulphonic or carboxylic acid groupings. They are usually precipitated by a calcium, barium or aluminum salt onto a substrate. Typical examples are peacock blue lake (CI Pigment Blue 24) and Persian orange (lake of CI Acid Orange 7), Black M Toner (GAF) (a mixture of carbon black and black dye precipitated on a lake).

A dark particle of the dyed type may be constructed from any light absorbing material, such as carbon black, or inorganic black materials. The dark material may also be selectively absorbing. For example, a dark green pigment may be used. Black particles may also be formed by staining latices with metal oxides, such latex copolymers consisting of any of butadiene, styrene, isoprene, methacrylic acid, methyl methacrylate, acrylonitrile, vinyl chloride, acrylic acid, sodium styrene sulfonate, vinyl acetate, chlorostyrene, dimethylaminopropylmethacrylamide, isocyanoethyl methacrylate and N-(isobutoxymethacrylamide), and optionally including conjugated diene compounds such as diacrylate, triacrylate, dimethylacrylate and trimethacrylate. Black particles may also be formed by a dispersion polymerization technique.

In the systems containing pigments and polymers, the pigments and polymers may form multiple domains within the electrophoretic particle, or be aggregates of smaller pigment/polymer combined particles. Alternatively, a central pigment core may be surrounded by a polymer shell. The pigment, polymer, or both can contain a dye. The optical purpose of the particle may be to scatter light, absorb light, or both. Useful sizes may range from 1 nm up to about 100 µm, as long as the particles are smaller than the bounding capsule. The density of the electrophoretic particle may be substantially matched to that of the suspending (i.e., electrophoretic) fluid. As defined herein, a suspending fluid has a density that is "substantially matched" to the density of the particle if the difference in their respective densities is between about zero and about two grams/milliliter ("g/ml"). This difference is preferably between about zero and about 0.5 g/ml.

Useful polymers for the particles include, but are not limited to: polystyrene, polyethylene, polypropylene, phenolic resins, du Pont Elvax resins (ethylene-vinyl acetate copolymers), polyesters, polyacrylates, polymethacrylates, ethylene acrylic acid or methacrylic acid copolymers (Nucrel Resins du Pont, Primacor Resins Dow Chemical), acrylic copolymers and terpolymers (Elvacite Resins du Pont) and PMMA. Useful materials for homopolymer/pigment phase separation in high shear melt include, but are not limited to, polyethylene, polypropylene, poly(methyl methacrylate), poly(isobutyl methacrylate), polystyrene, polybutadiene, polyisoprene, polyisobutylene, poly(lauryl methacrylate), poly(stearyl methacrylate), poly(isobornyl methacrylate), poly(t-butyl methacrylate), poly(ethyl methacrylate), poly(methyl acrylate), poly(ethyl acrylate), polyacrylonitrile, and copolymers of two or more of these materials. Some useful pigment/polymer complexes that are commercially available include, but are not limited to, Process Magenta PM 1776 (Magruder Color Company, Inc., Elizabeth, N.J.), Methyl Violet PMA VM6223 (Magruder Color Company, Inc., Elizabeth, N.J.), and Naphthol FGR RF6257 (Magruder Color Company, Inc., Elizabeth, N.J.).

The pigment-polymer composite may be formed by a physical process, (e.g., attrition or ball milling), a chemical process (e.g., microencapsulation or dispersion polymerization), or any other process known in the art of particle production. For example, the processes and materials for both the fabrication of liquid toner particles and the charging of those particles may be relevant.

New and useful electrophoretic particles may still be discovered, but a number of particles already known to those skilled in the art of electrophoretic displays and liquid toners can also prove useful. In general, the polymer requirements for liquid toners and encapsulated electrophoretic inks are similar, in that the pigment or dye must be easily incorporated therein, either by a physical, chemical, or physicochemical process, may aid in the colloidal stability, and may contain charging sites or may be able to incorporate materials which contain charging sites. One general requirement from the liquid toner industry that is not shared by encapsulated electrophoretic inks is that the toner must be capable of "fixing" the image, i.e., heat fusing together to create a uniform film after the deposition of the toner particles.

Typical manufacturing techniques for particles may be drawn from the liquid toner and other arts and include ball milling, attrition, jet milling, etc. The process will be illustrated for the case of a pigmented polymeric particle. In such a case the pigment is compounded in the polymer, usually in some kind of high shear mechanism such as a screw extruder. The composite material is then (wet or dry) ground to a starting size of around 10 μm. It is then dispersed in a carrier liquid, for example ISOPAR (Registered Trade Mark); (Exxon, Houston, Tex.), optionally with some charge control agent(s), and milled under high shear for several hours down to a final particle size and/or size distribution.

Another manufacturing technique for particles is to add the polymer, pigment, and suspending fluid to a media mill. The mill is started and simultaneously heated to a temperature at which the polymer swells substantially with the solvent. This temperature is typically near 100° C. In this state, the pigment is easily encapsulated into the swollen polymer. After a suitable time, typically a few hours, the mill is gradually cooled back to ambient temperature while stirring. The milling may be continued for some time to achieve a small enough particle size, typically a few microns in diameter. The charging agents may be added at this time. Optionally, more suspending fluid may be added.

Chemical processes such as dispersion polymerization, mini- or micro-emulsion polymerization, suspension polymerization precipitation, phase separation, solvent evaporation, in situ polymerization, seeded emulsion polymerization, or any process which falls under the general category of microencapsulation may be used. A typical process of this type is a phase separation process wherein a dissolved polymeric material is precipitated out of solution onto a dispersed pigment surface through solvent dilution, evaporation, or a thermal change. Other processes include chemical means for staining polymeric latices, for example with metal oxides or dyes.

B. Suspending Fluid

The suspending fluid containing the particles can be chosen based on properties such as density, refractive index, and solubility. A preferred suspending fluid has a low dielectric constant (about 2), high volume resistivity (about $10^{15}$ ohm-cm), low viscosity (less than 5 centistokes ("cst")), low toxicity and environmental impact, low water solubility (less than 10 parts per million ("ppm")), high specific gravity (greater than 1.5), a high boiling point (greater than 90° C.), and a low refractive index (less than 1.2).

The choice of suspending fluid may be based on concerns of chemical inertness, density matching to the electrophoretic particle, or chemical compatibility with both the electrophoretic particle and bounding capsule. The viscosity of the fluid should be low when movement of the particles is desired. The refractive index of the suspending fluid may also be substantially matched to that of the particles. As used herein, the refractive index of a suspending fluid is "substantially matched" to that of a particle if the difference between their respective refractive indices is between about zero and about 0.3, and is preferably between about 0.05 and about 0.2.

Additionally, the fluid may be chosen to be a poor solvent for some polymers; such a poor solvent is advantageous for use in the fabrication of microparticles, because it increases the range of polymeric materials useful in fabricating particles of polymers and pigments. Organic solvents, such as halogenated organic solvents, saturated linear or branched hydrocarbons, silicone oils, and low molecular weight halogen-containing polymers are some useful suspending fluids. The suspending fluid may comprise a single fluid. The fluid will, however, often be a blend of more than one fluid in order to tune its chemical and physical properties. Furthermore, the fluid may contain surface modifiers to modify the surface energy or charge of the electrophoretic particle or bounding capsule. Reactants or solvents for the microencapsulation process (oil soluble monomers, for example) can also be contained in the suspending fluid. Charge control agents can also be added to the suspending fluid.

Useful organic solvents include, but are not limited to, epoxides, such as decane epoxide and dodecane epoxide; vinyl ethers, such as cyclohexyl vinyl ether and Decave (Registered Trade Mark) (International Flavors & Fragrances, Inc., New York, N.Y.); and aromatic hydrocarbons, such as toluene and naphthalene. Useful halogenated organic solvents include, but are not limited to, tetrafluorodibromoethylene, tetrachloroethylene, trifluorochloroethylene, 1,2,4-trichlorobenzene and carbon tetrachloride. These materials have high densities. Useful hydrocarbons include, but are not limited to, dodecane, tetradecane, the aliphatic hydrocarbons in the Isopar (Registered Trade Mark) series (Exxon, Houston, Tex.), Norpar (Registered Trade Mark) (a series of normal paraffinic liquids), Shell-Sol (Registered Trade Mark) (Shell, Houston, Tex.), and Sol-Trol (Registered Trade Mark) (Shell), naphtha, and other petroleum solvents. These materials usually have low densities. Useful examples of silicone oils include, but are not limited to, octamethyl cyclosiloxane and higher molecular weight cyclic siloxanes, poly(methyl phenyl siloxane), hexamethyldisiloxane, and polydimethylsiloxane. These materials usually have low densities. Useful low molecular weight halogen-containing polymers include, but are not limited to, poly(chlorotrifluoroethylene) polymer (Halogenated Hydrocarbon Inc., River Edge, N.J.), Galden (Registered Trade Mark) (a perfluorinated ether from Ausimont, Morristown, N.J.), or Krytox (Registered Trade Mark) from du Pont (Wilmington, Del.). In a preferred embodiment, the suspending fluid is a poly(chlorotrifluoroethylene) polymer. In a particularly preferred embodiment, this polymer has a degree of polymerization from about 2 to about 10. Many of the above materials are available in a range of viscosities, densities, and boiling points.

The fluid must be capable of being formed into small droplets prior to a capsule being formed. Processes for forming small droplets include flow-through jets, membranes, nozzles, or orifices, as well as shear-based emulsifying schemes. The formation of small drops may be assisted by electrical or sonic fields. Surfactants and polymers can be used to aid in the stabilization and emulsification of the droplets in the case of an emulsion type encapsulation. One surfactant for use in displays of the invention is sodium dodecylsulfate.

It can be advantageous in some displays for the suspending fluid to contain an optically absorbing dye. This dye must be soluble in the fluid, but will generally be insoluble in the other components of the capsule. There is much flexibility in the choice of dye material. The dye can be a pure compound, or blends of dyes to achieve a particular color, including black.

The dyes can be fluorescent, which would produce a display in which the fluorescence properties depend on the position of the particles. The dyes can be photoactive, changing to another color or becoming colorless upon irradiation with either visible or ultraviolet light, providing another means for obtaining an optical response. Dyes could also be polymerizable by, for example, thermal, photochemical or chemical diffusion processes, forming a solid absorbing polymer inside the bounding shell.

There are many dyes that can be used in encapsulated electrophoretic displays. Properties important here include light fastness, solubility in the suspending liquid, color, and cost. These dyes are generally chosen from the classes of azo, anthraquinone, and triphenylmethane type dyes and may be chemically modified so as to increase their solubility in the oil phase and reduce their adsorption by the particle surface.

A number of dyes already known to those skilled in the art of electrophoretic displays will prove useful. Useful azo dyes include, but are not limited to: the Oil Red dyes, and the Sudan Red and Sudan Black series of dyes. Useful anthraquinone dyes include, but are not limited to: the Oil Blue dyes, and the Macrolex Blue series of dyes. Useful triphenylmethane dyes include, but are not limited to, Michler's hydrol, Malachite Green, Crystal Violet, and Auramine O.

The ratio of particles to suspending fluid to suspending fluid may vary over a wide range depending upon, inter alia, the density and opacity of the particles, the desired switching speed of the display and the degree of bistability desired. Typically, the particles will comprise from about 0.5 per cent to about 20 per cent by weight of the internal phase. However, in some dual particle systems, it may be advantageous to use substantially higher particle loadings in order to enhance the bistability of the images produced. Dual particle electrophoretic media in which the two types of particles carry charges of opposite polarity flocculate naturally because of the electrostatic attraction between the oppositely charged particles. At high particles loadings, with the particles constituting around 50 to 70 weight per cent of the internal phase, the resultant floc structure essentially fills the volume of the internal phase and holds the particles close to their addressed state (i.e., close to the positions which they occupy after an electric field has been applied to the medium for a period sufficient to drive the display to one of its two extreme optical states), thus enhancing the bistability of the display. The density, strength and rate of flocculation are readily controlled by adjusting particle charge, size and steric barrier thickness and composition. This method of increasing by increasing particle loading has the advantage that no extraneous material is added to the internal phase, and that the floc structure will stabilize not only the two extreme optical states but also the intermediate gray states. Also, this method reduces the temperature sensitivity of the stable states and reduces sticking of the particles to the capsule walls. The Bingham viscosity of the internal phase remains low, and even small floc volumes will aid in maintaining image bistability. Finally, the floc structure is easily broken by a short alternating current pulse, which can readily be applied before the direct current pulse used to alter the optical state of the display.

C. Charge Control Agents and Particle Stabilizers

Charge control agents are used to provide good electrophoretic mobility to the electrophoretic particles. Stabilizers are used to prevent agglomeration of the electrophoretic particles, as well as prevent the electrophoretic particles from irreversibly depositing onto the capsule wall. Either component can be constructed from materials across a wide range of molecular weights (low molecular weight, oligomeric, or polymeric), and may be a single pure compound or a mixture. The charge control agent used to modify and/or stabilize the particle surface charge is applied as generally known in the arts of liquid toners, electrophoretic displays, non-aqueous paint dispersions, and engine-oil additives. In all of these arts, charging species may be added to non-aqueous media in order to increase electrophoretic mobility or increase electrostatic stabilization. The materials can improve steric stabilization as well. Different theories of charging are postulated, including selective ion adsorption, proton transfer, and contact electrification.

An optional charge control agent or charge director may be used. These constituents typically consist of low molecular weight surfactants, polymeric agents, or blends of one or more components and serve to stabilize or otherwise modify the sign and/or magnitude of the charge on the electrophoretic particles. The charging properties of the pigment itself may be accounted for by taking into account the acidic or basic surface properties of the pigment, or the charging sites may take place on the carrier resin surface (if present), or a combination of the two. Additional pigment properties which may be relevant are the particle size distribution, the chemical composition, and the lightfastness.

Charge adjuvants may also be added. These materials increase the effectiveness of the charge control agents or charge directors. The charge adjuvant may be a polyhydroxy compound or an aminoalcohol compound, and is preferably soluble in the suspending fluid in an amount of at least 2% by weight. Examples of polyhydroxy compounds which contain at least two hydroxyl groups include, but are not limited to, ethylene glycol, 2,4,7,9-tetramethyldecyne-4,7-diol, poly(propylene glycol), pentaethylene glycol, tripropylene glycol, triethylene glycol, glycerol, pentaerythritol, glycerol tris(12-hydroxystearate), propylene glycerol monohydroxystearate, and ethylene glycol monohydroxystearate. Examples of aminoalcohol compounds which contain at least one alcohol function and one amine function in the same molecule include, but are not limited to, triisopropanolamine, triethanolamine, ethanolamine, 3-aminophenol, 5-amino-1-pentanol, and tetrakis(2-hydroxyethyl)ethylene diamine. The charge adjuvant is preferably present in the suspending fluid in an amount of about 1 to about 100 milligrams per gram ("mg/g") of the particle mass, and more preferably about 50 to about 200 mg/g.

The surface of the particle may also be chemically modified to aid dispersion, to improve surface charge, and to improve the stability of the dispersion, for example. Surface modifiers include organic siloxanes, organohalogen silanes and other functional silane coupling agents (Dow Corning (Registered Trade Mark) Z-6070, Z-6124, and 3 additive, Midland, Mich.); organic titanates and zirconates (Tyzor (Registered Trade Mark) TOT, TBT, and TE Series, du Pont); hydrophobing agents, such as long chain (C12 to $C_{50}$) alkyl and alkyl benzene sulphonic acids, fatty amines or diamines and their salts or quaternary derivatives; and amphipathic polymers which can be covalently bonded to the particle surface.

In general, it is believed that charging results as an acid-base reaction between some moiety present in the continuous phase and the particle surface. Thus useful materials are those which are capable of participating in such a reaction, or any other charging reaction as known in the art.

Different non-limiting classes of charge control agents which are useful include organic sulfates or sulfonates, metal soaps, block or comb copolymers, organic amides, organic zwitterions, and organic phosphates and phosphonates. Useful organic sulfates and sulfonates include, but are not limited to, sodium bis(2-ethylhexyl) sulfosuccinate, calcium dodecylbenzenesulfonate, calcium petroleum sulfonate, neutral or basic barium dinonylnaphthalene sulfonate, neutral or basic calcium dinonylnaphthalene sulfonate, dodecylbenzenesulfonic acid sodium salt, and ammonium lauryl sulfate. Useful metal soaps include, but are not limited to, basic or neutral barium petronate, calcium petronate, Co-, Ca-, Cu-, Mn-, Ni-, Zn-, and Fe- salts of naphthenic acid, Ba-, Al-, Zn-, Cu-, Pb-, and Fe- salts of stearic acid, divalent and trivalent metal carboxylates, such as aluminum tristearate, aluminum octanoate, lithium heptanoate, iron stearate, iron distearate, barium stearate, chromium stearate, magnesium octanoate, calcium stearate, iron naphthenate, zinc naphthenate, Mn- and Znheptanoate, and Ba-, Al-, Co-, Mn-, and Zn- octanoate. Useful block or comb copolymers include, but are not limited to, AB diblock copolymers of (A) polymers of 2-(N,N-dimethylamino) ethyl methacrylate quaternized with methyl p-toluene-sulfonate and (B) poly(2-ethylhexyl methacrylate), and comb graft copolymers with oil soluble tails of poly(12-hydroxystearic acid) and having a molecular weight of about 1800, pendant on an oil-soluble anchor group of poly (methyl methacrylate-methacrylic acid). Useful organic amides include, but are not limited to, polyisobutylene succinimides such as OLOA 371 and 1200, N-vinylpyrrolidone polymers and other polyamine condensates, such as Solsperse 13940 and 17000. Useful organic zwitterions include, but are not limited to, lecithin. Useful organic phosphates and phosphonates include, but are not limited to, the sodium salts of phosphated mono- and di-glycerides with saturated and unsaturated acid substituents.

Particle dispersion stabilizers may be added to prevent particle flocculation or attachment to the capsule walls. For the typical high resistivity liquids used as suspending fluids in electrophoretic displays, non-aqueous surfactants may be used. These include, but are not limited to, glycol ethers, acetylenic glycols, alkanolamides, sorbitol derivatives, alkyl amines, quaternary amines, imidazolines, dialkyl oxides, and sulfosuccinates.

D. Encapsulation

Encapsulation of the internal phase may be accomplished in a number of different ways. Numerous suitable procedures for microencapsulation are detailed in both Microencapsulation, Processes and Applications, (I. E. Vandegaer, ed.), Plenum Press, New York, N.Y. (1974) and Gutcho, Microcapsules and Microencapsulation Techniques, Noyes Data Corp., Park Ridge, N.J. (1976). The processes fall into several general categories, all of which can be applied to the present invention: interfacial polymerization, in situ polymerization, physical processes, such as coextrusion and other phase separation processes, in-liquid curing, and simple/complex coacervation.

Numerous materials and processes should prove useful in formulating displays of the present invention. Useful materials for simple coacervation processes to form the capsule include, but are not limited to, gelatin, poly(vinyl alcohol), poly(vinyl acetate), and cellulosic derivatives, such as, for example, carboxymethylcellulose. Useful materials for complex coacervation processes include, but are not limited to, gelatin, acacia, carageenan, carboxymethylcellulose, hydrolyzed styrene anhydride copolymers, agar, alginate, casein, albumin, methyl vinyl ether co-maleic anhydride, and cellulose phthalate. Useful materials for phase separation processes include, but are not limited to, polystyrene, poly (methyl methacrylate) (PMMA), poly(ethyl methacrylate), poly(butyl methacrylate), ethyl cellulose, poly(vinylpyridine), and polyacrylonitrile. Useful materials for in situ polymerization processes include, but are not limited to, polyhydroxyamides, with aldehydes, melamine, or urea and formaldehyde; water-soluble oligomers of the condensate of melamine, or urea and formaldehyde; and vinyl monomers, such as, for example, styrene, methyl methacrylate (MMA) and acrylonitrile. Finally, useful materials for interfacial polymerization processes include, but are not limited to, diacyl chlorides, such as, for example, sebacoyl, adipoyl, and di- or poly- amines or alcohols, and isocyanates. Useful emulsion polymerization materials may include, but are not limited to, styrene, vinyl acetate, acrylic acid, butyl acrylate, t-butyl acrylate, methyl methacrylate, and butyl methacrylate.

Capsules produced may be dispersed into a curable carrier, resulting in an ink which may be printed or coated on large and arbitrarily shaped or curved surfaces using conventional printing and coating techniques.

In the context of the present invention, one skilled in the art will select an encapsulation procedure and wall material based on the desired capsule properties. These properties include the distribution of capsule radii; electrical, mechanical, diffusion, and optical properties of the capsule wall; and chemical compatibility with the internal phase of the capsule.

The capsule wall generally has a high electrical resistivity. Although it is possible to use walls with relatively low resistivities, this may limit performance in requiring relatively higher addressing voltages. The capsule wall should also be mechanically strong (although if the finished capsule powder is to be dispersed in a curable polymeric binder for coating, mechanical strength is not as critical). The capsule wall should generally not be porous. If, however, it is desired to use an encapsulation procedure that produces porous capsules, these can be overcoated in a post-processing step (i.e., a second encapsulation). Moreover, if the capsules are to be dispersed in a curable binder, the binder will serve to close the pores. The capsule walls should be optically clear. The wall material may, however, be chosen to match the refractive index of the internal phase of the capsule (i.e., the suspending fluid) or a binder in which the capsules are to be dispersed. For some applications (e.g., interposition between two fixed electrodes), monodispersed capsule radii are desirable.

An encapsulation technique that is suited to the present invention involves a polymerization between urea and formaldehyde in an aqueous phase of an oil/water emulsion in the presence of a negatively charged, carboxyl-substituted, linear hydrocarbon polyelectrolyte material. The resulting capsule wall is a urea/formaldehyde copolymer, which discretely encloses the internal phase. The capsule is clear, mechanically strong, and has good resistivity properties.

The related technique of in situ polymerization utilizes an oil/water emulsion, which is formed by dispersing the electrophoretic fluid (i.e., the dielectric liquid containing a suspension of the pigment particles) in an aqueous environment. The monomers polymerize to form a polymer with higher affinity for the internal phase than for the aqueous phase, thus condensing around the emulsified oily droplets. In one in situ polymerization process, urea and formaldehyde condense in the presence of poly(acrylic acid) (see, e.g., U.S. Pat. No. 4,001,140). In other processes, described in U.S. Pat. No. 4,273,672, any of a variety of cross-linking agents borne in aqueous solution is deposited around microscopic oil droplets. Such cross-linking agents include aldehydes, especially formaldehyde, glyoxal, or glutaraldehyde; alum; zirconium salts; and polyisocyanates.

The coacervation approach also utilizes an oil/water emulsion. One or more colloids are coacervated (i.e., agglomerated) out of the aqueous phase and deposited as shells around the oily droplets through control of temperature, pH and/or relative concentrations, thereby creating the microcapsule. Materials suitable for coacervation include gelatins and gum arabic. See, e.g., U.S. Pat. No. 2,800,457.

The interfacial polymerization approach relies on the presence of an oil-soluble monomer in the electrophoretic composition, which once again is present as an emulsion in an aqueous phase. The monomers in the minute hydrophobic droplets react with a monomer introduced into the aqueous phase, polymerizing at the interface between the droplets and the surrounding aqueous medium and forming shells around the droplets. Although the resulting walls are relatively thin and may be permeable, this process does not require the elevated temperatures characteristic of some other processes, and therefore affords greater flexibility in terms of choosing the dielectric liquid.

Coating aids can be used to improve the uniformity and quality of the coated or printed electrophoretic ink material. Wetting agents are typically added to adjust the interfacial tension at the coating/substrate interface and to adjust the liquid/air surface tension. Wetting agents include, but are not limited to, anionic and cationic surfactants, and nonionic species, such as silicone or fluoropolymer-based materials. Dispersing agents may be used to modify the interfacial tension between the capsules and binder, providing control over flocculation and particle settling.

Surface tension modifiers can be added to adjust the air/ink interfacial tension. Polysiloxanes are typically used in such an application to improve surface leveling while minimizing other defects within the coating. Surface tension modifiers include, but are not limited to, fluorinated surfactants, such as, for example, the Zonyl (Registered Trade Mark) series from du Pont, the Fluorad (Registered Trade Mark) series from 3M (St. Paul, Minn.), and the fluoroalkyl series from Autochem (Glen Rock, N.J.); siloxanes, such as, for example, Silwet (Registered Trade Mark) from Union Carbide (Danbury, Conn.); and polyethoxy and polypropoxy alcohols. Antifoams, such as silicone and silicone-free polymeric materials, may be added to enhance the movement of air from within the ink to the surface and to facilitate the rupture of bubbles at the coating surface. Other useful antifoams include, but are not limited to, glyceryl esters, polyhydric alcohols, compounded antifoams, such as oil solutions of alkylbenzenes, natural fats, fatty acids, and metallic soaps, and silicone antifoaming agents made from the combination of dimethyl siloxane polymers and silica. Stabilizers such as UV-absorbers and antioxidants may also be added to improve the lifetime of the ink.

E. Binder Material

The binder typically is used as an adhesive medium that supports and protects the capsules, as well as binds the electrode materials to the capsule dispersion. A binder can be non-conducting, semiconductive, or conductive. Binders are available in many forms and chemical types. Among these are water-soluble polymers, water-borne polymers, oil-soluble polymers, thermoset and thermoplastic polymers, and radiation-cured polymers.

Among the water-soluble polymers are the various polysaccharides, the polyvinyl alcohols, N-methylpyrrolidone, N-vinylpyrrolidone, the various Carbowax (Registered Trade Mark) species (Union Carbide, Danbury, Conn.), and poly(2-hydroxyethyl acrylate).

The water-dispersed or water-borne systems are generally latex compositions, typified by the Neorez (Registered Trade Mark) and Neocryl (Registered Trade Mark) resins (Zeneca Resins, Wilmington, Mass.), Acrysol (Registered Trade Mark) (Rohm and Haas, Philadelphia, Pa.), Bayhydrol (Registered Trade Mark) (Bayer, Pittsburgh, Pa.), and the Cytec Industries (West Paterson, N.J.) HP line. These are generally latices of polyurethanes, occasionally compounded with one or more of the acrylics, polyesters, polycarbonates or silicones, each lending the final cured resin in a specific set of properties defined by glass transition temperature, degree of tack, softness, clarity, flexibility, water permeability and solvent resistance, elongation modulus and tensile strength, thermoplastic flow, and solids level. Some water-borne systems can be mixed with reactive monomers and catalyzed to form more complex resins. Some can be further cross-linked by the use of a cross-linking reagent, such as an aziridine, for example, which reacts with carboxyl groups.

A typical application of a water-borne resin and aqueous capsules follows. A volume of particles is centrifuged at low speed to separate excess water. After a given centrifugation process, for example 10 minutes at 60×gravity (g), the capsules are found at the bottom of the centrifuge tube, while the water is at the top. The water is carefully removed (by decanting or pipetting). The mass of the remaining capsules is measured, and a mass of resin is added such that the mass of resin is, for example, between one eighth and one tenth of the weight of the capsules. This mixture is gently mixed on an oscillating mixer for approximately one half hour. After about one half hour, the mixture is ready to be coated onto the appropriate substrate.

The thermoset systems are exemplified by the family of epoxies. These binary systems can vary greatly in viscosity, and the reactivity of the pair determines the pot life of the mixture. If the pot life is long enough to allow a coating operation, capsules may be coated in an ordered arrangement in a coating process prior to the resin curing and hardening.

Thermoplastic polymers, which are often polyesters, are molten at high temperatures. A typical application of this type of product is hot-melt glue. A dispersion of heat-resistant capsules could be coated in such a medium. The solidification process begins during cooling, and the final hardness, clarity and flexibility are affected by the branching and molecular weight of the polymer.

Oil or solvent-soluble polymers are often similar in composition to the water-borne system, with the obvious exception of the water itself. The latitude in formulation for solvent systems is enormous, limited only by solvent choices and polymer solubility. Of considerable concern in solvent-based systems is the viability of the capsule itself; the integrity of the capsule wall cannot be compromised in any way by the solvent.

Radiation cure resins are generally found among the solvent-based systems. Capsules may be dispersed in such a medium and coated, and the resin may then be cured by a timed exposure to a threshold level of ultraviolet radiation, either long or short wavelength. As in all cases of curing polymer resins, final properties are determined by the branching and molecular weights of the monomers, oligomers and cross-linkers.

A number of water-reducible monomers and oligomers are, however, marketed. In the strictest sense, they are not water soluble, but water is an acceptable diluent at low concentrations and can be dispersed relatively easily in the mixture. Under these circumstances, water is used to reduce the viscosity (initially from thousands to hundreds of thousands centipoise). Water-based capsules, such as those made from a protein or polysaccharide material, for example, could be dispersed in such a medium and coated, provided the viscosity could be sufficiently lowered. Curing in such systems is generally by ultraviolet radiation.

Like other encapsulated electrophoretic displays, the encapsulated electrophoretic displays of the present invention provide flexible, reflective displays that can be manufactured easily and consume little power (or no power in the case of bistable displays in certain states). Such displays, therefore, can be incorporated into a variety of applications and can take on many forms. Once the electric field is removed, the electrophoretic particles can be generally stable. Additionally, providing a subsequent electric charge can alter a prior configuration of particles. Such displays may include, for example, a plurality of anisotropic particles and a plurality of second particles in a suspending fluid. Application of a first electric field may cause the anisotropic particles to assume a specific orientation and present an optical property. Application of a second electric field may then cause the plurality of second particles to translate, thereby disorienting the anisotropic particles and disturbing the optical property. Alternatively, the orientation of the anisotropic particles may allow easier translation of the plurality of second particles. Alternatively or in addition, the particles may have a refractive index that substantially matches the refractive index of the suspending fluid.

An encapsulated electrophoretic display may take many forms. The capsules of such a display may be of any size or shape. The capsules may, for example, be spherical and may have diameters in the millimeter range or the micron range, but are preferably from about ten to about a few hundred microns. The particles within the capsules of such a display may be colored, luminescent, light-absorbing or transparent, for example.

The following Examples are now given, though by way of illustration only, to show details of particularly preferred reagents, conditions and techniques used in the electrophoretic media and displays of the present invention. All centrifuging mentioned was carried out on a Beckman GS-6 or Allegra 6 centrifuge (available from Beckman Coulter, Inc., Fullerton, Calif. 92834).

EXAMPLE 1

This Example illustrates the provision of a silica coating on specularly reflective particles comprising a family of pigments known to those skilled in the art as pearlescent pigments, which may be used in the present media and displays. The procedure used is adapted from U.S. Pat. No. 3,639,133.

Mearlin MagnaPearl pigment (titania on a mica surface, 50 g, particle size range of about 2 to 10 μm; the material used was Mearlin MagnaPearl 3100, available from Engelhard Corporation, Pigments and Additives Group, Iselin, N.J., 08830-0770—"Mearlin MagnaPearl" is a Registered Trade Mark) was placed in a sodium silicate solution (415 of a 0.073M solution with 1.9% sodium hydroxide), and the resultant mixture was vigorously shaken in a plastic bottle and then sonicated for 1 hour at 30-35° C. The suspension was then heated to 90-95° C. over a period of 1 hour and sulfuric acid (150 ml of a 0.22M solution) and additional sodium silicate (80 ml of a 1.17M solution with 0.28% sodium hydroxide) were added simultaneously over a period of about 2 to 3 hours, with rapid stirring. After these additions had been completed, the reaction mixture was stirred for an additional 15 minutes, then cooled slowly to room temperature, added to plastic bottles and centrifuged at 3500 rpm for 15 minutes. The supernatant liquor was decanted, and the silica-coated pigment re-dispersed in deionized water and centrifuged at 3500 rpm for 15 minutes. The washing was repeated twice more, and the pigment finally dried in air for 24 hours, and then in an oven at 85° C. for 2 hours.

EXAMPLE 2

This Example illustrates reaction of the silica-coated pigment prepared in Example 1 with a bifunctional reagent in the first stage of a process to provide a positively-charged, polymer-coated specularly reflective particle useful in the electrophoretic media and displays of the present invention.

To a mixture of ethanol (1000 ml) and water (100 ml), concentrated ammonium hydroxide was added (about 12 ml) until the pH reached 9.0-9.5, N-[3-trimethoxysilyl)-propyl]-N'-(4-vinylbenzyl)ethylene diamine hydrochloride (40 g of a 40 weight per cent solution in methanol) was added, and the resultant solution was stirred rapidly for 4 minutes. The silica-coated Mearlin MagnaPearl 3100 pigment (50 g) prepared in Example 1 was then added, and the mixture stirred rapidly for 7 minutes. The resultant suspension was poured into plastic bottles and centrifuged at 3500 rpm for 30 minutes. The supernatant liquor was decanted, and the silanized pigment re-dispersed in ethanol and centrifuged at 3500 rpm on the same centrifuge for 30 minutes, and the liquid decanted. The washing was repeated, and the pigment finally dried in air for 18 hours, then under vacuum at 70° C. for 2 hours.

EXAMPLE 3

This Example illustrates reaction of the silica-coated pigment prepared in Example 1 with a bifunctional reagent in the first stage of a process to provide a negatively charged, polymer-coated specularly reflective particle useful in the electrophoretic media and displays of the present invention.

To a mixture of ethanol (415) and water (35 ml), 33% acetic acid (about 18 ml) was added until the pH reached 4.5, trimethoxysilylpropyl methacrylate (20 ml) was added, and the resultant solution was stirred rapidly for 4 minutes. The silica-coated Mearlin MagnaPearl 3100 pigment (50 g) prepared in Example 1 was then added, and the mixture stirred rapidly for 7 minutes. The resultant suspension was poured into plastic bottles and centrifuged at 3500 rpm for 30 minutes. The supernatant liquor was decanted, and the silanized pigment re-dispersed in ethanol and centrifuged at 3500 rpm on the same centrifuge for 30 minutes, and the liquid decanted. The washing was repeated, and the pigment finally dried in air for 18 hours, then under vacuum at 70° C. for 2 hours.

EXAMPLE 4

This Example illustrates conversion of the silanized pigment produced in Example 3 to the corresponding polymer-coated specularly reflective pigment.

The silanized pigment produced in Example 3 (50 g) was placed in a round-bottomed flask with toluene (50 g) and lauryl methacrylate (50 g). The resultant mixture was stirred rapidly under a nitrogen atmosphere (argon may alternatively be used) for 20 minutes, then slowly heated to 50° C. and AIBN (0.5 g in 10 ml of toluene) added quickly. The suspension was then heated to 65° C. and stirred at this temperature under nitrogen for a further 18 hours. The resultant viscous suspension was poured into plastic bottles, the flask being washed out with ethyl acetate to remove residual product and the ethyl acetate solution added to the bottles. The bottles were centrifuged at 3500 rpm for 30 minutes. The supernatant liquor was decanted, and the polymer-coated pigment re-dispersed in ethyl acetate and centrifuged at 3500 rpm for 30 minutes, and the liquid decanted. The washing was repeated, and the pigment dried in air until a workable powder was obtained, and then under vacuum at 65° C. for 6 to 18 hours.

EXAMPLE 5

This Example illustrates the preparation of a polymer-coated carbon black useful in the electrophoretic media and displays of the present invention.

Part A: Preparation of Black Pigment having Radical Grafting Groups Attached to the Particle Surface Carbon black (Printex A, 140 g) was dispersed in water (3 L) with magnetic stirring, then hydrochloric acid (6 ml of 37% by weight) and 4-vinylaniline (3.0 g, 25 mmol) were added, and the resultant mixture was heated to 40° C. Separately, sodium nitrite (1.74 g, 25 mmol) was dissolved in water (10 ml). This nitrite solution was then added slowly to the carbon black-containing reaction mixture over a 10 minute period, and the reaction mixture was stirred for a further 16 hours. The resultant product was centrifuged and the solids produced rinsed with acetone (200 ml). This rinsing was repeated and the solids dried under vacuum for 12 hours to produce 141 g of the desired product. Thermogravimetric analysis of this product showed a 1.4 per cent weight loss.

Part B: Preparation of the Polymer-coated Black Pigment

To a reaction flask fitted with a nitrogen purge apparatus, magnetic stir bar and reflux column were added the product of Part A above (20 g), toluene (40 ml), 2-ethylhexyl-methacrylate (40 ml) and AIBN (0.26 g). The flask was purged with nitrogen for 20 minutes with stirring, then immersed into a room temperature oil bath, gradually heated to 70° C., with continuous stirring, and maintained at this temperature for 20 hours. The reaction mixture was then allowed to cool, diluted with an equal volume of acetone and centrifuged. The supernatant liquor was decanted, and the solids redispersed in THF (ethyl acetate may alternatively be used) and rinsed; this process was repeated until thermogravimetric analysis consistently indicated a weight loss of 8.9 per cent. Approximately 20 g of the final product was isolated.

EXAMPLE 6

This Example illustrates the construction of an encapsulated dual particle display using the polymer-coated pigments prepared in Examples 4 and 5.

The suspending fluid used is a mixture of a 1:1 w/w mixture of a hydrocarbon (Isopar-G, available commercially from Exxon Corporation, Houston, Tex.; "Isopar" is a Registered Trade Mark) and a halogenated hydrocarbon oil (Halogenated hydrocarbon oil 1.8, available commercially from Halogenated Hydrocarbon Products Corporation, River Edge, New Jersey referred to hereinafter for simplicity as "Halocarbon"); this mixture is hereinafter referred to as "1:1 Isopar/Halocarbon mixture". The suspending fluid contains Solsperse 17000 (available commercially from Avecia Ltd., Blackley, Manchester, United Kingdom; "Solsperse" is a Registered Trade Mark) as a charge control agent, and Span 85 (sold by ICI Americas, Inc., Wilmington, Del.; "Span" is a Registered Trade Mark) as a dispersant.

Part A: Preparation of Internal Phase

To make approximately 100 ml of internal phase ready for encapsulation, there were used 4.210 g of polymer-coated Mearlin MagnaPearl 3100 prepared in Example 5 above and 0.227 g of polymer-coated carbon black prepared in Example 7 above. These pigments were mixed with Solsperse 17000 dispersant (0.444 g. added in the form of a10 w/w % solution in Isopar G), Span 85 dispersant (0.444 g) and the 1:1 w/w Isopar/Halocarbon mixture (99.112 g). The resultant solution was well shaken and stored on a roll mill for at least 24 hours before being used in the encapsulation process.

Part B: Encapsulation

The internal phase thus prepared was then encapsulated using a reactor equipped with a water jacket, an overhead stirrer, a dropping funnel and a pH meter. Gelatin (4.5 g was dissolved in deionized water (262.2 g) at 40° C. with stirring, care being taken to ensure that no foam was produced on the surface of the solution. Separately, acacia (3.33 g) was dissolved in deionized water (65.56 g) and the resultant solution heated to 40° C. Also separately, the internal phase described above was heated to 40° C. and then added to the gelatin solution; the gelatin solution was stirred during the addition, which was conducted by introducing the internal phase through the dropping funnel, the outlet of which was placed below the surface of the gelatin solution. After the addition of the internal phase was complete, the rate of stirring was increased and the stirring continued for 30 minutes at 40° C. in order to emulsify the internal phase into droplets having an average diameter of about 200 µm.

The acacia solution was then added over a period of about 1 minute, care being taken to avoid foaming. The pH of the mixture was lowered to 4.82 using 10 per cent aqueous acetic acid, and the vigorous stirring was continued to a further40 minutes at the same temperature. The temperature of the mixture was lowered to 10° C. over a period of two hours, with continued vigorous stirring, and glutaraldehyde (1.7 g) was added. After this addition, the mixture was gradually warmed to 25° C. and stirred vigorously overnight. Finally, stirring was discontinued, and the mixture was allowed to settle for 10-15 minutes, during which time a foamy mixture separated on top of the liquid.

The liquid phase was then removed, leaving the foamy mixture in the reactor, and the capsules in this liquid phase washed three times by sedimentation and redispersion in deionized water. The capsules were separated by size to yield a distribution between 100 and 300 µm diameter, with a mean diameter of about 200 µm; such a distribution can be effected by hand sieving the capsules to produce the final capsule slurry.

Part C: Production of Electrophoretic Display

The resulting capsule slurry was centrifuged and then mixed with an aqueous urethane binder (NeoRez R-9320) at a ratio of 1 part by weight binder to 9 parts by weight of capsules, and 0.3 weight per cent of hydroxypropylmethyl-cellulose was added as a slot-coating additive. The resultant mixture was slot coated on to a 125 µm thick indium-tin oxide coated polyester film moving at 1 m/sec relative to the slot coating head. The coated film was allowed to air dry for 10 minutes, then oven dried at 50° C. for 15 minutes to produce an electrophoretic medium approximately 50 µm thick containing essentially a single layer of capsules (see the aforementioned published International Patent Application WO 00/20922).

To provide an experimental electrophoretic display, comprising only a single pixel, which could be used to investigate the properties of the electrophoretic medium thus prepared, the capsule-coated surface of the coated film was then overcoated with the aforementioned NeoRez R-9320 binder using a doctor blade with a 13 mil (330 μm) gap setting (this binder serves both to planarize the capsule-coated surface and as a lamination adhesive) and the overcoated film dried at 50° C. for 20 minutes. The dried film was then hot laminated to a second polyester film coated, on the side facing the electrophoretic medium, with indium tin oxide to produce the final electrophoretic display.

The resulting dual particle display could be switched between its black and specularly reflective states in not more than 500 msec by applying a voltage of 42 V across the indium tin oxide electrode.

Numerous changes and modifications can be made in the preferred embodiments of the present invention already described without departing from the spirit and skill of the invention. For example, although the embodiments of the invention illustrated in the accompanying drawings all use specularly reflective pigments which are also electrophoretically mobile, the displays of the present invention may also use specularly reflective pigments which are not electrophoretically mobile. Such displays would have "free-floating" pigments comprising non-electrophoretically mobile specularly reflective pigments combined with electrophoretically mobile pigments. The "free-floating" pigments may enhance the brightness of either color in a two-particle, two-color display. Similarly, although the invention has been described with reference to encapsulated electrophoretic displays, it can readily be used in non-encapsulated displays. Numerous other possible modifications of the illustrated embodiments will be apparent to those skilled in electrophoretic display technology. Accordingly, the foregoing description is to be construed in an illustrative and not in a limitative sense.

The invention claimed is:

1. An electrophoretic medium comprising a plurality of at least one type of particles suspended in a suspending fluid and capable of moving therethrough on application of an electric field to the medium, the particles including at least one electrophoretically mobile specularly reflective particle.

2. An electrophoretic medium according to claim 1 comprising a single type of electrophoretically mobile, specularly reflective particle in a colored suspending fluid.

3. An electrophoretic medium according to claim 1 wherein the specularly reflective, electrophoretically mobile particle has a first optical characteristic, and the medium further comprises a second type of particle which has a charge of opposite polarity to that of the first particle and is electrophoretically mobile, and has a second optical characteristic different from the first optical characteristic.

4. An electrophoretic medium according to claim 3 wherein the second type of particle comprises carbon black.

5. An electrophoretic medium according to claim 4 wherein the carbon black particles bear a polymer coating.

6. An electrophoretic medium according to claim 3 wherein the suspending fluid is substantially uncolored.

7. An electrophoretic medium according to claim 3 further comprising a third type of particle which has a charge of the same polarity as the specularly reflective particle, is not specularly reflective, and is electrophoretically mobile.

8. An electrophoretic medium according to claim 7 wherein the third type of particle comprises titania.

9. An electrophoretic medium according to claim 8 wherein the titania particles bear a polymer coating.

10. An electrophoretic medium according to claim 7 wherein the third type of particle has a higher electrophoretic mobility than the specularly reflective particle.

11. An electrophoretic medium according to claim 7 further comprising a fourth type of particle which has a charge of the same polarity as that of the second type of particle, is electrophoretically mobile, and is specularly reflective.

12. An electrophoretic medium according to claim 1 further comprising a second type of particle which has a charge of the same polarity as that of the specularly reflective particle but has a higher electrophoretic mobility than the specularly reflective particle.

13. An electrophoretic medium according to claim 12 wherein the second type of particle has a first optical characteristic, the electrophoretic medium further comprising a third type of particle which has a charge of the opposite polarity to that of the second type of particle, is electrophoretically mobile, and has a second optical characteristic different from the first optical characteristic.

14. An electrophoretic medium according to claim 1 wherein said specularly reflective particle comprises one or more of aluminum, platinum, palladium, silver, gold, nickel, copper, chromium titanium, zinc, iron, stainless steel, tungsten, molded and polished plastic chips, bismuth oxychloride (BiOCl), mica ($CaCO_3$), or titania ($TiO_2$) or iron oxide ($Fe_2O_3$) particles adhered to the surface of mica or bismuth oxychloride.

15. An electrophoretic medium according to claim 1 wherein the specularly reflective particle has an aspect ratio of at least 3.

16. An electrophoretic medium according to claim 15 wherein the specularly reflective particle has an aspect ratio in the range of about 5 to about 25.

17. An electrophoretic medium according to claim 1 wherein the specularly reflective particle has a major axis length of about 1 μm to about 15 μm.

18. An electrophoretic medium according to claim 1 comprising at least one capsule having a capsule wall encapsulating the at least one type of particles and the suspending fluid.

19. An electrophoretic medium according to claim 1 comprising a substrate having a plurality of closed cells formed therein, the at least one type of particles and the suspending fluid being retained in the closed cells.

20. An electrophoretic display comprising an electrophoretic medium according to claim 1 and at least one electrode disposed adjacent to the electrophoretic medium.

* * * * *